(12) United States Patent
Ryan et al.

(10) Patent No.: US 8,784,536 B2
(45) Date of Patent: *Jul. 22, 2014

(54) METAL-ORGANIC FRAMEWORKS FOR XE/KR SEPARATION

(71) Applicant: Northwestern University, Evanston, IL (US)

(72) Inventors: Patrick J. Ryan, Vernon Hills, IL (US); Omar K. Farha, Morton Grove, IL (US); Linda J. Broadbelt, Glenview, IL (US); Randall Q. Snurr, Evanston, IL (US); Youn-Sang Bae, Evanston, IL (US)

(73) Assignee: Northwestern University, Evanstone, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/974,406

(22) Filed: Aug. 23, 2013

(65) Prior Publication Data

US 2014/0013943 A1 Jan. 16, 2014

Related U.S. Application Data

(63) Continuation of application No. 13/199,043, filed on Aug. 17, 2011, now Pat. No. 8,518,153.

(60) Provisional application No. 61/401,816, filed on Aug. 19, 2010.

(51) Int. Cl.
*B01D 53/02* (2006.01)

(52) U.S. Cl.
USPC .............................. 95/127; 502/401; 556/115

(58) Field of Classification Search
USPC .............................. 95/127; 502/401; 556/115
See application file for complete search history.

(56) References Cited

U.S. PATENT DOCUMENTS

| | | | |
|---|---|---|---|
| 7,553,352 | B2 | 6/2009 | Mueller et al. |
| 8,518,153 | B2 | 8/2013 | Ryan et al. |
| 2006/0099398 | A1 | 5/2006 | Hesse et al. |
| 2006/0185388 | A1 | 8/2006 | Muller et al. |
| 2006/0252641 | A1 | 11/2006 | Yaghi et al. |
| 2007/0248852 | A1 | 10/2007 | Mueller et al. |
| 2008/0190289 | A1 | 8/2008 | Mueller et al. |
| 2008/0227634 | A1 | 9/2008 | Muller et al. |
| 2009/0000474 | A1 | 1/2009 | Macgillivray |

OTHER PUBLICATIONS

Adsorption and Separation of Noble Gases by IRMOF-1: Grand Canonical Monte Carlo Simulations; Greathouse et al. Ind. Eng. Chem. Res. 2009, 48, 3425-3431 (2009).*
Greathouse et al., Sandia Report, Sand 2008-6687, Oct. 2008.
Bae et al., "Enhancement of $CO_2/N_2$ Selectivity in a Metal-Organic Framework by Cavity Modification," J. Mater. Chem., 2009, 19, pp. 2131-2134.
Bae et al., "Separation of $CO_2$ from $CH_4$ Using Mixed-Ligand Metal-Organic Frameworks," Langmuir, 2008, 24, pp. 8592-8598.
Bohlmann et al., "Characteristics of the Metal-Organic Framework Compound $Cu_3$ (benzene 1, 3, 5-tricarboxylate)$_2$ by Means of $^{129}$Xe Nuclear Magnetic and Electron Paramagnetic Resonance Spectroscopy," J. Phys. Chem., B 2006, 110, pp. 20177-20181.
International Preliminary Report on Patentability, International Application No. PCT/US2011/001439, Feb. 19, 2013.
Chen et al., "High $H_2$ Adsorption in a Microporous Metal-Organic Framework with Open Metal Sites," Angew. Chem. Int. Ed., 2005, 44, pp. 4745-4749.
Cho et al., "A Metal-Organic Framework Material That Functions as an Enantioselective Catalyst for Olefin Epoxidation," Chem. Commun., 2006, pp. 2563-2565.
Chui et al., "A Chemically Functionalizable Nanoporous Material $[Cu_3 (TMA)_2 (H_2O)_3]_n$," Science 283, 1999, pp. 1148-1150.
Duren et al., "Using Molecular Simulation to Characterize Metal-Organic Frameworks for Adsorption Applications," Chem. Soc. Rev., 2009, 38, pp. 1237-1247.
Ryan et al., "Is Catenation Beneficial for Hydrogen Storage in Metal-Organic Frameworks?" Chem. Commun., 2008, pp. 4132-4134.
Eddaoudi et al., "Systematic Design of Pore Size and Functionality in Isoreticular MOFs and Their Application in Methane Storage," Science 295, 2002, pp. 469-472.
Ferey, "Hybrid Porous Solids: Past, Present, Future," Chem. Soc. Rev., 2008, 37, pp. 191-214.
Frost et al., "Effects on Surface Area, Free Volume, and Heat of Adsorption on Hydrogen Uptake in Metal-Organic Frameworks," J. Phys. Chem. B, 2006, 110, pp. 9565-9570.
Greathouse et al., "Adsorption and Separation of Noble Gases by IRMOF-1: Grand Canonical Monte Carlo Simulations," Ind. Eng. Chem. Res. 2009, 48, pp. 3425-3431.
Hartmann et al., "Adsorptive Separation of Isobutene and Isobutane on $Cu_3 (BTC)_2$," Langmuir, 2008, 24, pp. 8634-8642.
Hirscher, "Hydrogen Storage in Metal-Organic Frameworks," Scripta Materialia 56, 2007, pp. 809-812.
Jameson et al., "Competitive Adsorption of Xenon and Krypton in Zeolite NaA: $^{129}$Xe Nuclear Magnetic Resonance Studies and Grand Canonical Monte Carlo Simulations," J. Chem. Phys. 107, 1997, pp. 4364-4372.

(Continued)

*Primary Examiner* — Christopher P Jones
(74) *Attorney, Agent, or Firm* — The Marbury Law Group PLLC

(57) ABSTRACT

Metal-organic framework (MOF) materials are provided and are selectively adsorbent to xenon (Xe) over another noble gas such as krypton (Kr) and/or argon (Ar) as a result of having framework voids (pores) sized to this end. MOF materials having pores that are capable of accommodating a Xe atom but have a small enough pore size to receive no more than one Xe atom are desired to preferentially adsorb Xe over Kr in a multi-component (Xe—Kr mixture) adsorption method. The MOF material has 20% or more, preferably 40% or more, of the total pore volume in a pore size range of 0.45-0.75 nm which can selectively adsorb Xe over Kr in a multi-component Xe—Kr mixture over a pressure range of 0.01 to 1.0 MPa.

5 Claims, 22 Drawing Sheets

(56) References Cited

OTHER PUBLICATIONS

Keffer, "Effect of Loading and Nanopore Shape on Binary Adsorption Selectivity," J. Phys. Chem., 1996, 100, pp. 638-645.

Kitagawa et al., "Functional Porous Coordination Polymers," Andew. Chem. Int. Ed. 2004, 43, pp. 2334-2375.

Lee et al., "Metal-Organic Framework Materials as Catalysts," Chem., Soc. Rev., 2009, 38, pp. 1450-1459.

Li, "Selective Gas Adsorption and Separation in Metal-Organic Frameworks," Chem. Soc. Rev., 2009, 38, pp. 1477-1504.

Lin et al., "High Capacity Hydrogen Adsorption in Cu (II) Tetracarboxylate Framework Materials: The Role of Pore Size, Ligand Functionalization, and Exposed Metal Sites," J. Am. Chem. Soc., 2009, 131, pp. 2159-2171.

Lui et al., "Enhanced Adsorption Selectivity of Hydrogen Methane Mixtures in Metal-Organic Frameworks with Interpenetration: A Molecular Simulation Study," J. Phys. Chem. C 2008, 112, pp. 9854-9860.

Mayo et al., "DREIDING: A Generic Force Field for Molecular Simulations," J. Phys. Chem. 1990, 94, pp. 8897-8909.

Mueller et al., "Metal-Organic Frameworks—Prospective Industrial Applications," J. Mater. Chem., 2006, 16, pp. 626-636.

Murray et al., "Hydrogen Storage in Metal-Organic Frameworks," Chem. Soc. Rev., 2009, 38, pp. 1294-1314.

Murthi, "Effects of Molecular Siting and Adsorbent Heterogeneity on the Ideality of Adsorption Equilibria," Langmuir 2004, 20, pp. 2489-2497.

Myers et al., "Adsorption in Porous Materials at High Pressure: Theory and Experiment," Oct. 9, 2002, http://www.seas.upenn.edu/~amyers/langrev.pdf.

Pan et al., "Separation of Hydrocarbon with Microporous Metal-Organic Framework," Agnew. Chem. 2006, 118, pp. 632-635.

Park et al., "Exceptional Chemical and Thermal Stability of Zeolitic Imidazolate Framework," PNAS, vol. 103, 2006, pp. 10186-10191.

Rappe et al., "UFF, a Full Periodic Table Force Field for Molecular Mechanics and Molecular Dynamics Simulations," J. Am. Chem. Soc. 1992, 114, pp. 10024-10035.

Rowsell et al., "Strategies for Hydrogen Storage in Metal-Organic Frameworks," Angew. Chem. Int. Ed., 2005, 44, pp. 4670-4679.

Rowsell et al., "Metal-Organic Frameworks: A New Class of Porous Materials," Microporous and Mesoporous Materials 73, 2004, pp. 3-14.

Schultz et al., "A Catalytically Active, Permanently Micro-porous MOF with Metalloporphyrin Struts," J. Am. Chem. Soc. 2009, 131, pp. 4204-4205.

Talu, "Reference Potentials for Adsorption of Helium, Argon, Methane, and Krypton in High-Silica Zeolites," Colloids and Surfaces A: Physicochemical and Engineering Aspects 187-188, 2001, pp. 83-93.

Van Tassel, "Adsorption Simulations of Small Molecules and Their Mixtures in a Eolite Micropore," Langmuir 1994, 10, pp. 1257-1267.

Walton et al., "Understanding Inflections and Steps in Carbon Dioxide Adsorption Isotherms in Metal-Organic Frameworks," J. Am. Chem. Soc., 2008, 130, pp. 406-407.

Xamena et al., "MOFs as Catalysts: Activity, Reusability and Shape-Selectivity of a Pd-containing MOF," Journal of Catalysis 250, 2007, pp. 294-298.

Yang et al., "Molecular Simulation of Separation of $CO_2$ from Flue Gases in Cu-BTC Metal-Organic Framework," AIChE Journal, vol. 53, No. 11, Nov. 2007, pp. 2832-2840.

Yang et al., "Molecular Simulation of Carbon Dioxide/Methane/Hydrogen Mixture in Metal-Organic Frameworks," J. Phys. Chem. B, 2006, 110, pp. 17776-17783.

Yazaydin et al., "Enhanced $CO_2$ Adsorption in Metal-Organic Frameworks via Occupation of Open-Metal Sites by Coordinated Water Molecules," Chem. Mater., 2009, 21, pp. 1425-1430.

* cited by examiner

METAL-ORGANIC FRAMEWORKS FOR XE/KR SEPARATION

CONTRACTUAL ORIGIN OF THE INVENTION

This invention was made with government support under Grant No. DE-FG02-03ER15457 awarded by the Department of Energy. The government has certain rights in the invention.

RELATED APPLICATION

This application claims benefits and priority of U.S. provisional application Ser. No. 61/401,816 filed Aug. 19, 2010, the entire disclosure of which is incorporated herein by reference.

FIELD OF THE INVENTION

The present invention relates to separation of noble gases such as xenon and krypton using certain metal-organic framework (MOFs) materials.

BACKGROUND OF THE INVENTION

Separating xenon from krypton is an industrially important problem. Xenon (Xe) and krypton (Kr) are used in fluorescent light bulbs, and current technology produces these gases from the cryogenic distillation of air, in which these noble gases are present in small concentrations (1.14 ppmv Kr, 0.086 ppmv Xe). Both xenon and krypton separate into the oxygen-rich stream after distillation, and these gases are concentrated and purified to produce an 80/20 molar mixture of krypton to xenon.[1] This final mixture typically undergoes further cryogenic distillation to produce pure krypton and pure xenon. Distillation is an energy-intensive process, and separation of these gases by selective adsorption near room temperature would be much more energy efficient. Additionally, separating krypton from xenon is an important step in removing radioactive krypton-85 during treatment of spent nuclear fuel.[2] However, even after cryogenic distillation, trace levels of radioactive krypton in the xenon-rich phase are too high to permit further use.[2] If adsorbents could reduce krypton-85 concentrations in the xenon-rich phase to permissible levels, there could be an entirely new supply source of xenon for industrial use. Thus, there is a strong need to develop adsorbent materials for this separation to reduce energy consumption and to reuse byproducts of consumed nuclear fuel.

There are several examples in the literature where zeolites have been tested for Xe/Kr separation. Previous research has shown NaX zeolite to be a selective adsorbent for xenon over krypton with a selectivity of about 6 with krypton concentrations ranging from 1 to 10,000 ppm.[2] Jameson et al.[3] showed that NaA zeolite had a selectivity of approximately 4 for binary mixtures of xenon and krypton at 300 K between 1 and 10 bar. They also used molecular simulations to show that ideal adsorbed solution theory (IAST) could accurately predict the selectivities and mixture behavior from the single-component isotherms.

Metal-organic frameworks,[4-6] or MOFs, are a new class of nanoporous materials. Composed of organic linkers and metal corners, these materials self-assemble in solution to form stable, crystalline frameworks. Coordination bonds between oxygen and nitrogen atoms with metal centers allow for a variety of topologies, and choice of the organic linker allows one to tailor pore sizes and environments for particular applications. As a result, these materials have garnered much attention for hydrogen storage,[7-9] separations,[10,11] and catalysis.[12-14]

A number of groups have investigated MOFs for separation of other gases. For example, Bae et al.[15] used both experiments and simulation to show a mixed-ligand MOF effectively separates carbon dioxide from methane. Bae et al.[16] also showed that exchanging fluorinated-methylpyridine into a MOF could substantially increase the selectivity of carbon dioxide over nitrogen due to the increased polar environment. Pan et al.[17] synthesized a microporous MOF with 1D hydrophobic microchannels and demonstrated its ability to separate n-butane from other n-alkanes and olefins. Hartmann et al.[18] showed that isobutene can be separated from isobutane using HKUST-1 in a breakthrough system. Yang et al.[19,20] used molecular simulations to predict that HKUST-1 is a promising candidate for separation of carbon dioxide from both air and methane/hydrogen mixtures.

To date, there are a few publications that report the investigation of Xe/Kr separation using MOFs. Mueller et al.[21] measured noble gas adsorption in IRMOF-1 and noticed significantly higher adsorption for the heavier gases, namely xenon and krypton, in MOF-filled containers relative to containers without MOF material. Building on these results, they built a breakthrough system filled with HKUST-1 and showed that a 94/6 molar mixture of krypton/xenon could be purified to over 99% krypton and less than 50 ppm xenon. Greathouse et al.[22] recently simulated noble gas adsorption in IRMOF-1. They predicted that IRMOF-1 has a selectivity of about 2.5-3 for Xe over Kr at 298 K and pressures of both 1 and 10 bar.

SUMMARY OF THE INVENTION

The present invention envisions a method of separating a particular noble gas in a gas mixture by contacting the gas mixture with an adsorbent material comprising a metal-organic framework (MOF) material having framework pores that are sized to receive no more than one atom of the particular noble gas for selectively adsorbing the particular noble gas from the gas mixture. MOF materials having a relatively high percentage of pores (percentage of total pore volume) that are capable of accommodating the noble gas atom but that have a small enough pore size to receive no more than one such atom are desired to preferentially adsorb the particular noble gas over one or more other noble gases in a multi-component mixture adsorption method embodiment. However, the pore size cannot be so small that it significantly limits overall gas uptake (capacity), which is undesirable. The present invention thus envisions MOF adsorbent materials for separation of a particular noble gas and one or more other noble gases in a gas mixture.

In an illustrative embodiment of the invention, the present invention provides metal-organic framework (MOF) materials that are selectively adsorbent to xenon (Xe) over another noble gas, such as for example krypton (Kr) and/or argon (Ar), as a result of having a framework voids (pores) sized to this end. MOF materials having 20% or more, preferably 40% or more, of the total pore volume, capable of accommodating a Xe atom but having a small enough pore size to receive no more than one Xe atom are desired to preferentially adsorb Xe over Kr in a multi-component (Xe—Kr gas mixture) adsorption method. The present invention thus envisions MOF adsorbent materials for separation of xenon (Xe) and one or more other noble gases.

An illustrative Xe-selective MOF material includes characteristic multiple pore size categories within its particular framework wherein 20% or more, preferably 40% or more, of the total pore volume has a size in the range of 0.45-0.75 nm, which compares to the Lennard-Jones diameters of 0.4100 nm and 0.3636 nm for Xe and Kr, respectively. Such MOF materials can selectively adsorb Xe over another noble gas, such as Kr, in a multi-component gas mixture over a pressure range of 0.01 to 1.0 MPa.

In a particular illustrative embodiment of the present invention, a Xe-selective adsorbent material having a chemical formula unit represented by $Cu_2(3,3',5,5'$-biphenyltetracarboxylate) and having the NbO topology has been identified, tested and determined to exhibit increased xenon selectivity over a wider pressure range of 0.01 to 1.0 MPa compared to other MOFs materials. The material was found to exhibit a selectively of about 9 to about 11 in the pressure range of 0.1 to 1.0 MPa.

Advantages and detailed features of the present invention will become more apparent from the following detailed description taken with the following drawings.

DETAILED DESCRIPTION OF THE INVENTION

Figure 1:
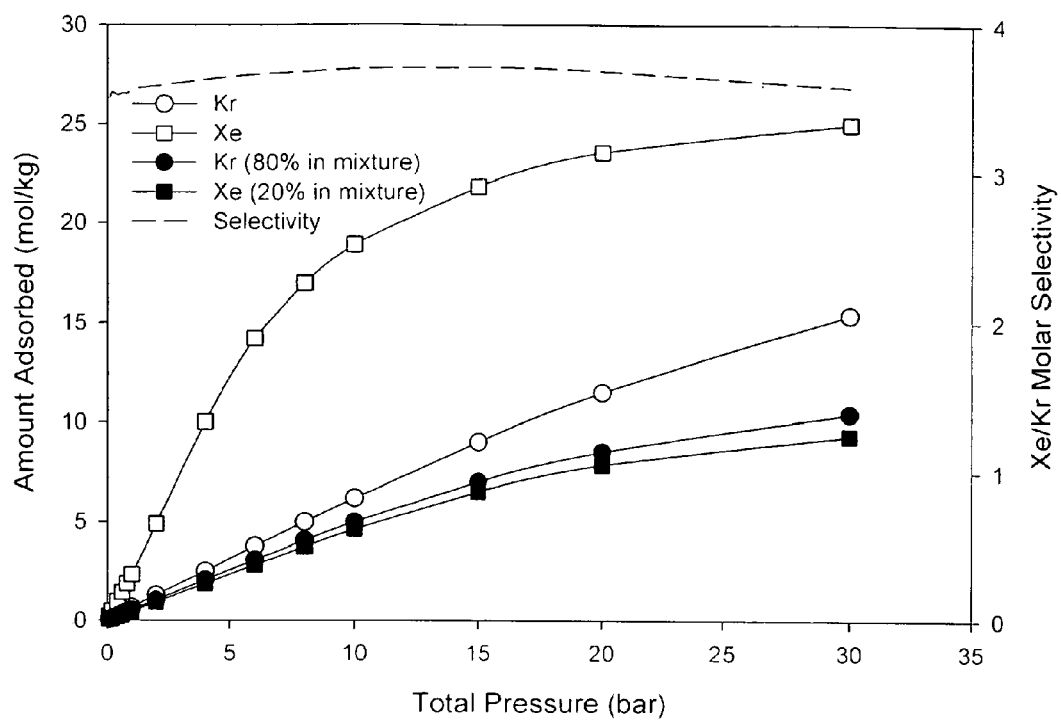
FIG. 1: Single-component (open symbols) and mixture (filled symbols) isotherms for Xe and Kr adsorption in UMCM-1 at 273 K.

The present invention provides metal-organic framework (MOF) materials that are selectively adsorbent to xenon (Xe) over another noble gas, such as for example krypton (Kr) and/or argon (Ar), as a result of having a framework voids (pores) sized to this end. MOF materials having 20% or more, preferably 40% or more, of the total pore volume capable of accommodating a Xe atom but having a small enough pore size to receive no more than one Xe atom are desired to preferentially adsorb Xe over Kr in a multi-component (Xe—Kr gas mixture) adsorption method. The present invention thus envisions particular MOF adsorbent materials for separation of xenon (Xe) and one or more other noble gases.

For purposes of illustration and not limitation, a number of MOFs with different pore sizes, linkers, metal atoms, and topologies were chosen in order to sample a variety of MOF properties and gain insight into which characteristics are desired for separation of Xe and one or more other noble gases, such as for example Kr and/or Ar. The selected MOFs are IRMOF-1,[23] UMCM-1,[24] ZIF-8,[25] HKUST-1,[26] MOF-505,[27] NOTT-101,[28] NOTT-108,[28] and Pd-MOF.[29] These MOFs are described in detail in the references noted by superscripts, the teachings of these references being incorporated herein by reference to this end. These MOF's were screened for xenon/krypton separation using grand canonical Monte Carlo (GCMC) simulations as described below.

The MOF designated MOF-505 was made for actual testing as described below after conduct of the screening.

MOF-505 Crystal Synthesis:

Make Solution A: 15 ml DMF with 8 drops of 15% $HBF_4$

Take:: 15 mg organic ligand (0.045 mmol)

65 mg $Cu(NO_3)_2*2.5H_2O$ (0.28 mmol)

2 ml of Solution A combine in 2 dram vials sonnicated heat in oven 90 degrees C. for 1 day yields light blue crystalline powder The chemical formula unit for each MOF is listed below in Table 1:

TABLE 1

Chemical formula Unit

| Material | Formula Unit |
|---|---|
| IRMOF-1 | $Zn_4O$(1,4-benzenedicarboxylate)$_3$ |
| UMCM-1 | $Zn_4O$(1,4-benzenedicarboxylate)(1,3,5-tris(4-benzenecarboxylate)benzene)$_{4/3}$ |
| ZIF-8 | Zn(2-methylimidazolate)$_2$ (Sodalite topology) |
| HKUST-1 | $Cu_3$(1,3,5-benzenetricarboxylate)$_2$ |
| MOF-505 | $Cu_2$(3,3',5,5'-biphenyltetracarboxylate) (NbO topology) |
| NOTT-101 | $Cu_2$(3,3'',5,5''-triphenyltetracarboxylate) |
| NOTT-108 | $Cu_2$(2',3',5',6'-tetrafluoro-3,3'',5,5''-triphenyltetracarboxylate) |
| Pd-MOF | Pd(2-hydroxypyrimidinolate)$_2$ |

Applicants calculated the pore size distribution for each of these MOFs. The pore size distribution of a MOF is calculated by randomly selecting a point within the unit cell volume (that does not overlap with framework atoms) and calculating the largest sphere that can fit within the MOF that includes that particular point. This process is repeated until the entire unit cell volume has been sampled sufficiently. The distribution is then plotted as a function of the sphere radius. A detailed description of this process is provided by Gelb L D, Gubbins, K E, Pore size distribution in porous glasses: A computer simulation study, *Langmuir*, 1999; 15; 305-308, the teachings of which are incorporated herein by reference.

The results are summarized in Table 2.

TABLE 2

Pore diameters of all MOFs investigated estimated from pore size distribution calculations.

| MOF | Pore Sizes (nm) | | |
|---|---|---|---|
| IRMOF-1 | 1.12 | 1.45 | |
| UMCM-1 | 1.03 | 1.39 | 2.33 |
| ZIF-8 | 1.05 | | |
| HKUST-1 | 0.50 | 1.06 | 1.24 |
| MOF-505 | 0.48 | 0.71 | 0.95 |
| NOTT-101 | 0.50 | 0.96 | 1.05 |
| NOTT-108 | 0.45 | 0.89 | 1.05 |
| Pd-MOF | 0.22 | 0.49 | 0.58 |

Figure 9:
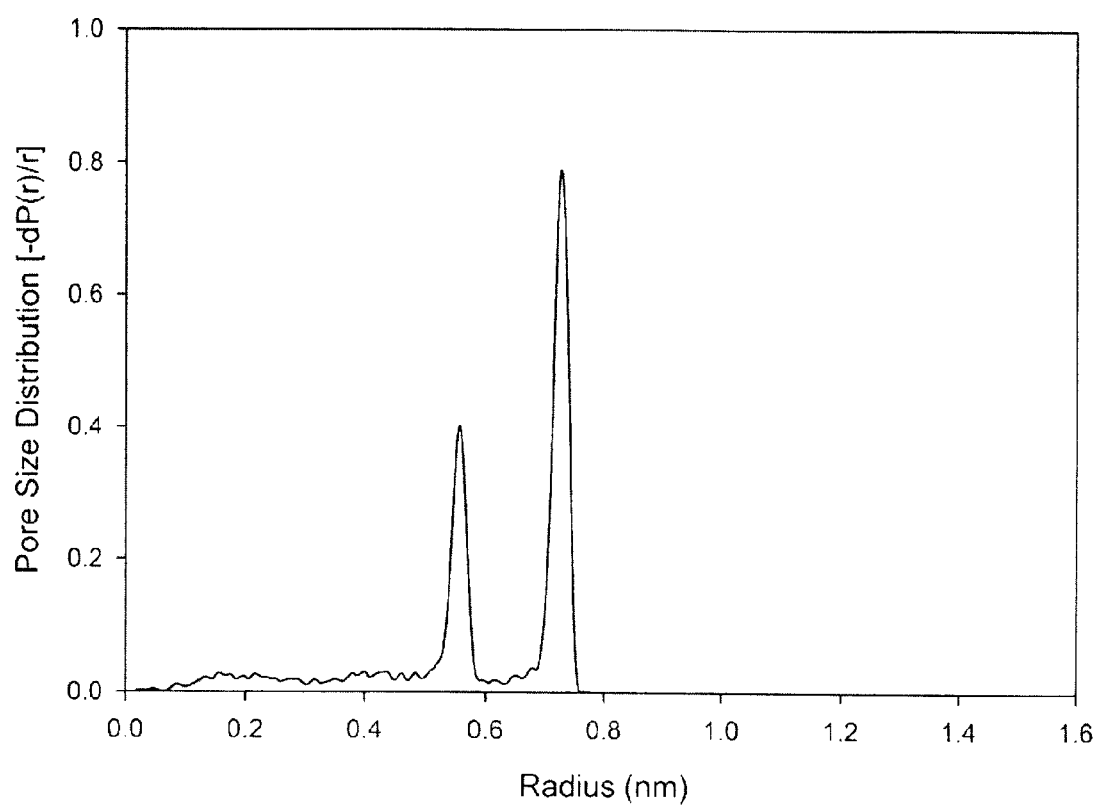
FIG. 9: Pore size distribution for IRMOF-1 where [−dP(r)/r] on the vertical axis means the fraction of pores having radius r and Radius (nm) on the horizontal axis corresponds to the radius of framework pores.
Figure 12:
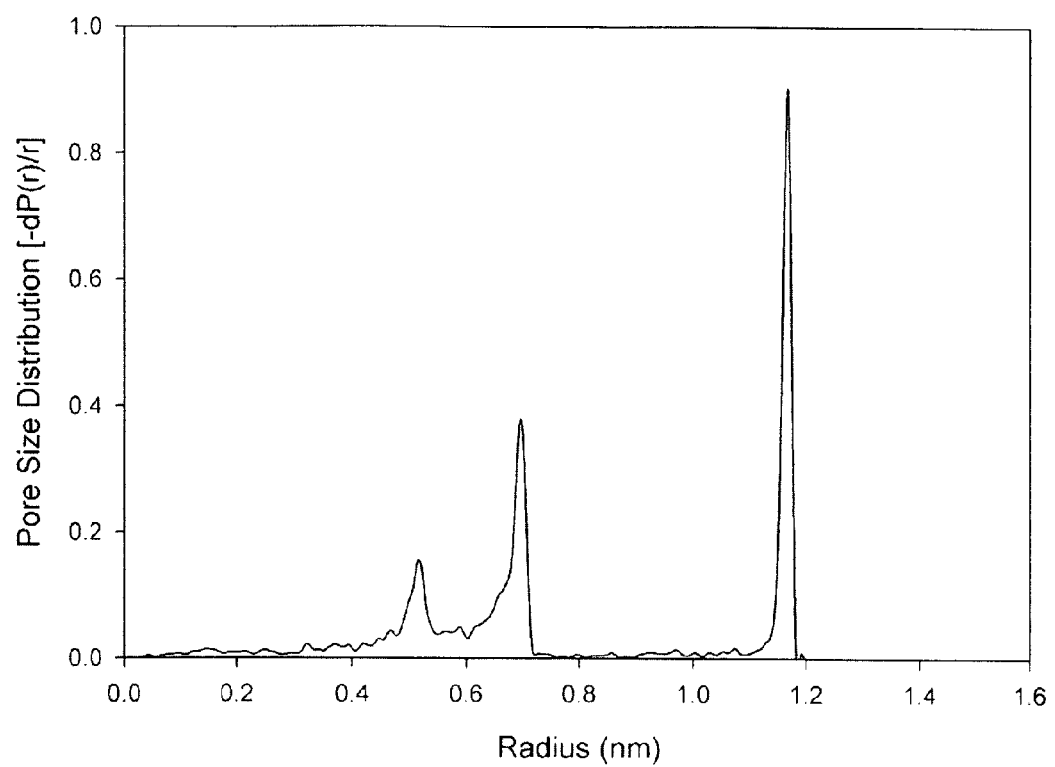
FIG. 12: Pore size distribution for UMCM-1.
Figure 14:
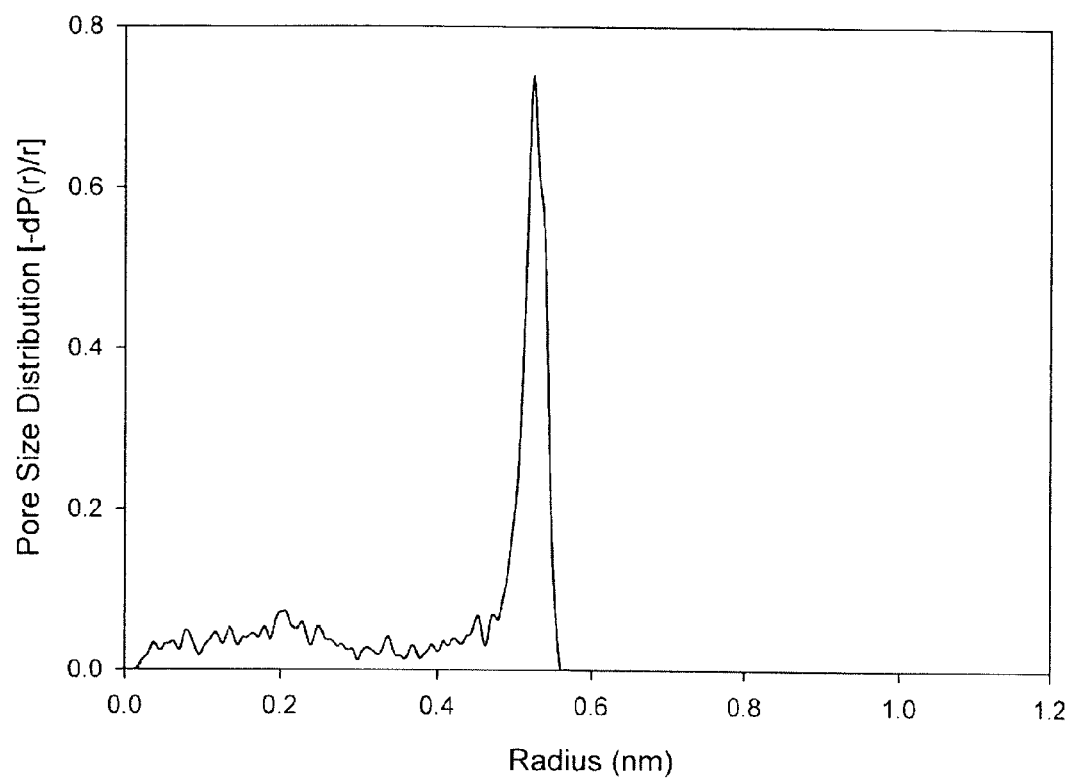
FIG. 14: Pore size distribution for ZIF-8.
Figure 17:
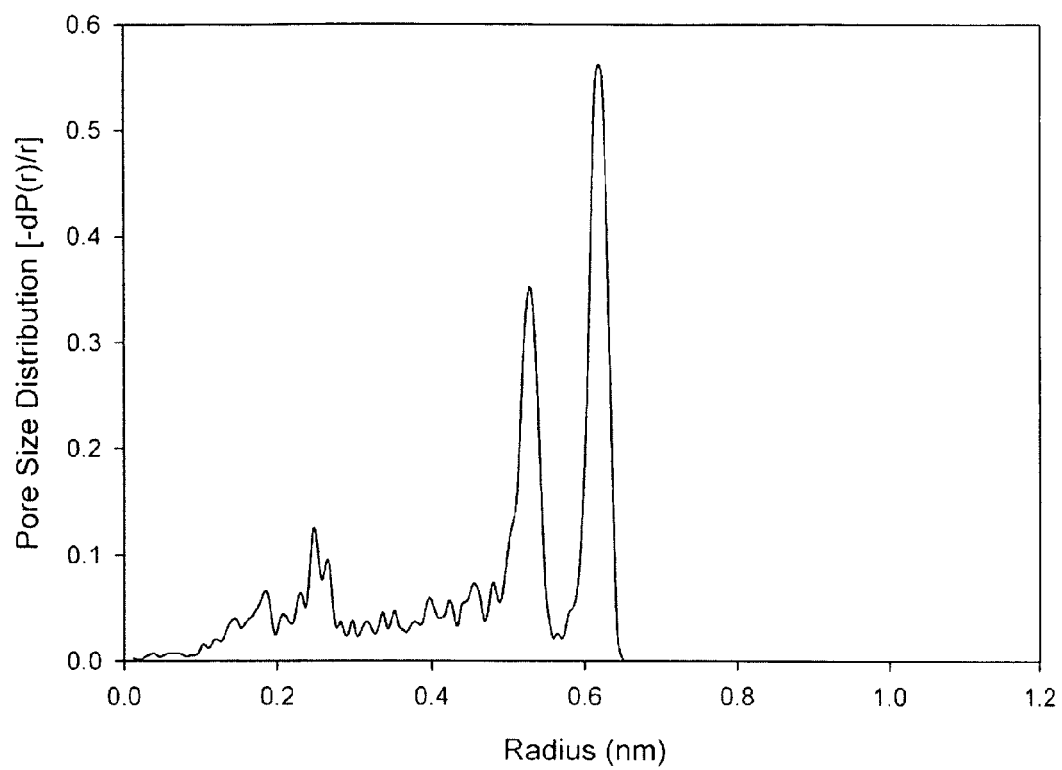
FIG. 17: Pore size distribution for HKUST-1.
Figure 18:
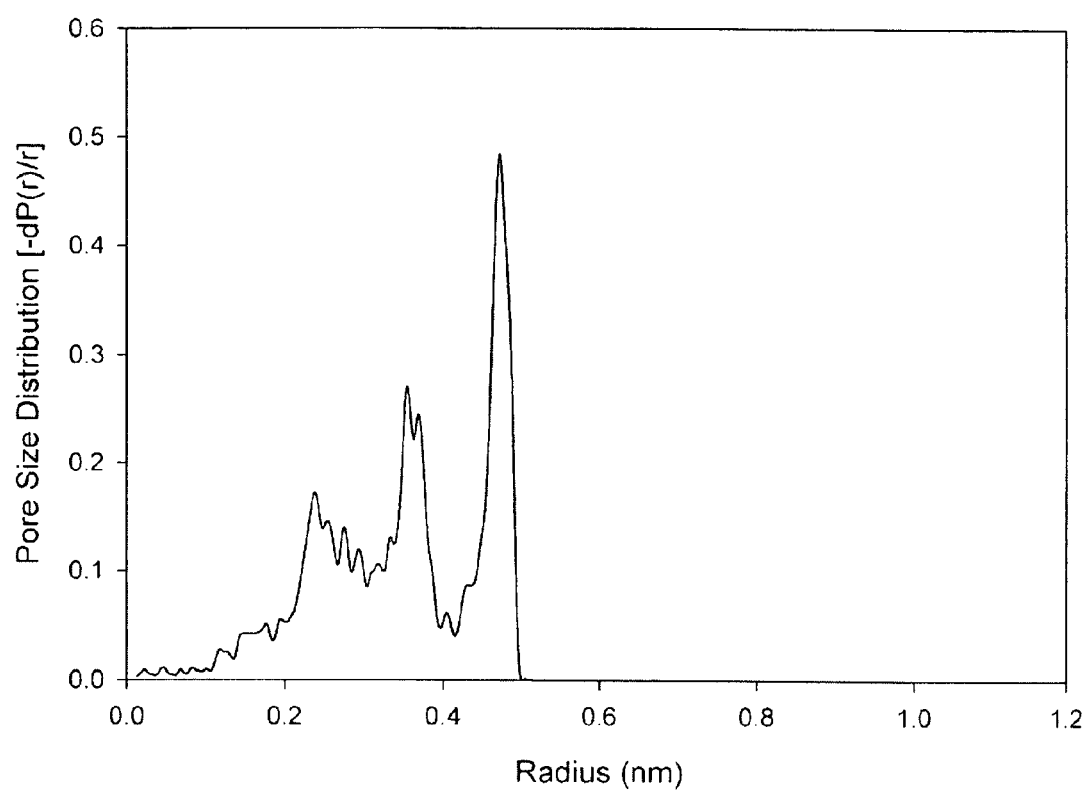
FIG. 18: Pore size distribution for MOF-505.
Figure 19:
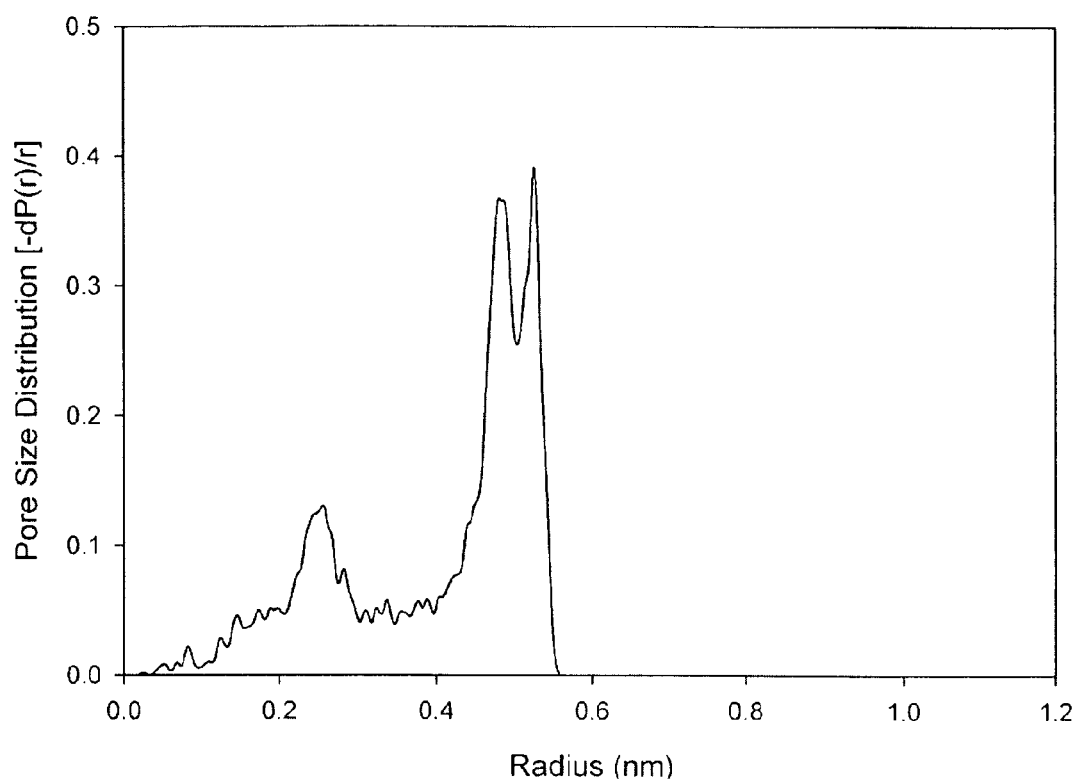
FIG. 19: Pore size distribution for NOTT-101.
Figure 20:
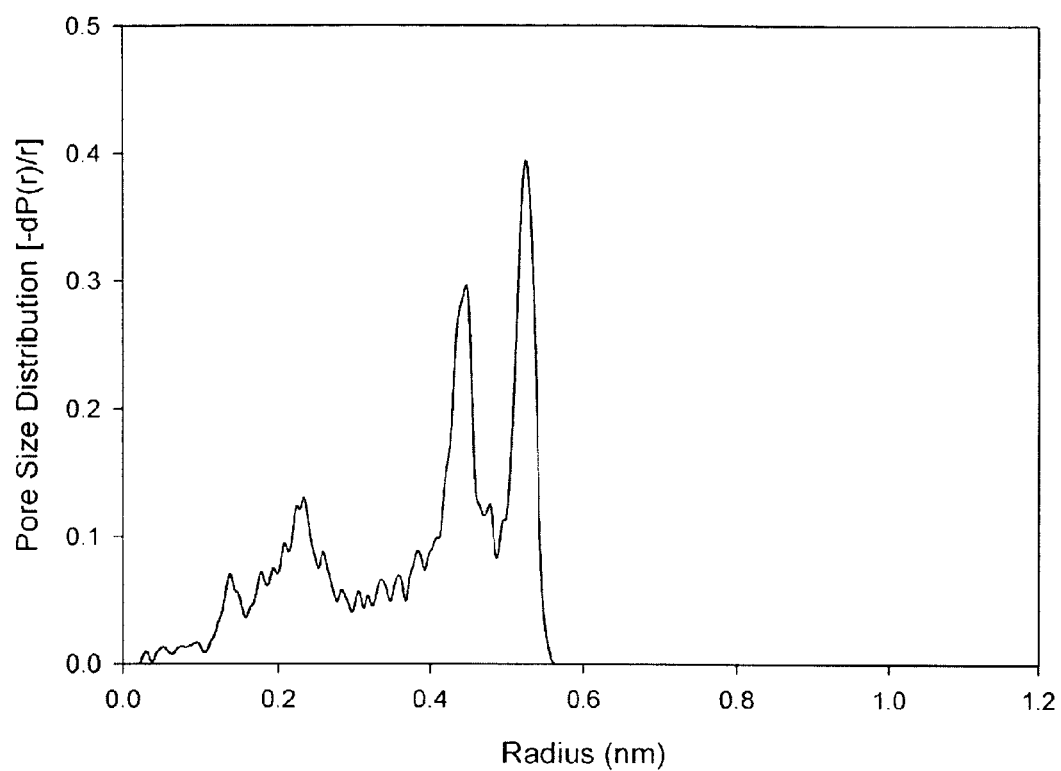
FIG. 20: Pore size distribution for NOTT-108.
Figure 22:
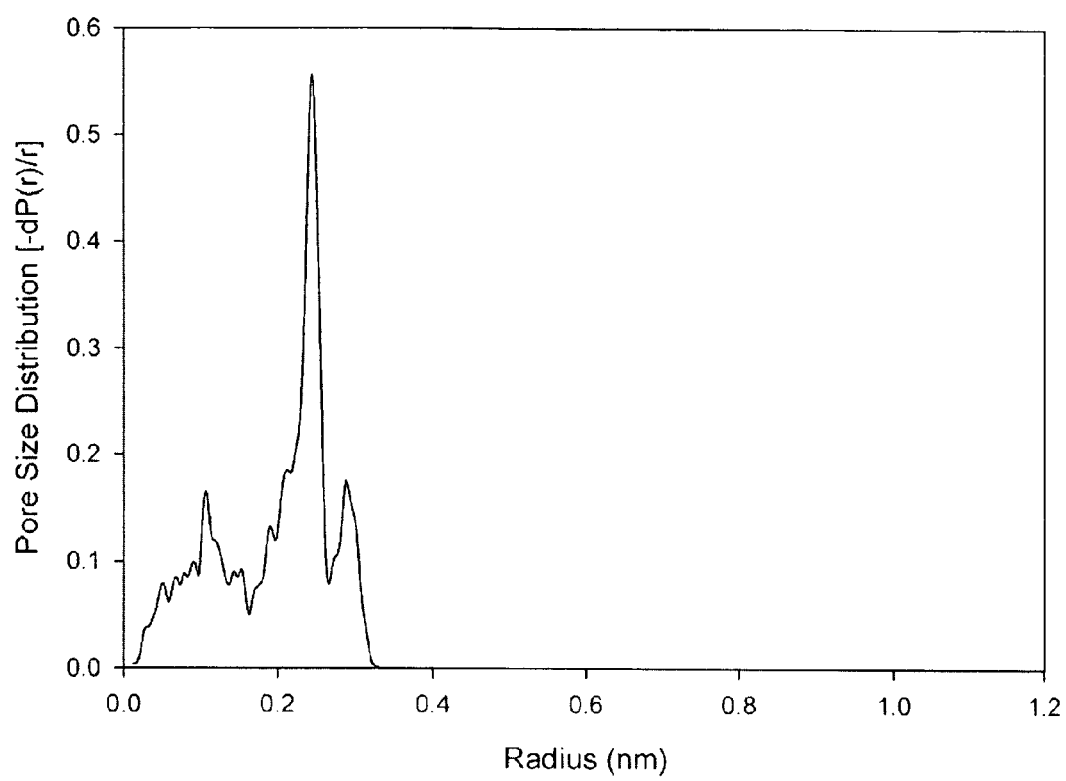
FIG. 22: Pore size distribution for Pd-MOF.

IRMOF-1 is composed of $Zn_4O$ corners and benzenedicarboxylate (BDC) linkers and has large pore diameters of 1.12 and 1.45 nm. FIG. 9. UMCM-1 also has $Zn_4O$ corners but has two organic linkers: BDC and 1,3,5-tris(4-carboxyphenyl) benzene (BTB). This MOF contains both microporous and mesoporous cavities or pores, FIG. 12. Zeolitic-imidazolate-framework #8 (ZIF-8) contains tetrahedral $Zn^{2+}$ atoms coordinated to methylimidazolate linkers in a sodalite-type framework. Its main cavity or pore spans 1.05 nm across, FIG. 14. HKUST-1 is made of copper paddlewheels with benzenetricarboxylate (BTC) linkers, which form both small and large pockets or pores. The smaller pockets or pores have diameters of 0.50 nm, while the larger pockets or pores have diameters of 1.06 and 1.24 nm, FIG. 17. The window into these small pockets or pores is approximately 0.46 nm, and previous experimental work using $^{129}$Xe NMR spectroscopy[30] has demonstrated that these sites are accessible to xenon. Based on the size of krypton and xenon, whose Lennard-Jones diameters are 0.3636 and 0.4100 nm, respectively, these pockets or pores should be accessible as adsorption sites. However, only about 12% of the total pore volume has the small size (0.50 nm pore diameter). MOF-505 is composed of $Cu^{2+}$ paddlewheels coordinated to biphenyltetracarboxylate linkers and has characteristic pores of 0.48, 0.71, and 0.95 nm diameter where about 46% of the total pore volume is in the range of 0.45-0.75 nm, FIG. 18. Similar to MOF-505, NOTT-101 uses $Cu^{2+}$ paddlewheels with triphenyltetracarboxylate linkers and results in slightly larger pores of 0.50, 0.96, and 1.05 nm diameter, FIG. 19. NOTT-108 is identical to NOTT-101 with the exception of four fluorine atoms in the place of hydrogens on the middle phenyl moiety of the triphenyl linker. The pore distribution of NOTT-108 is shown in FIG. 20. Since the NOTT-101 crystal structure was not published in the original paper, applicants constructed a NOTT-101 structure by using the NOTT-108 structure and manually changing fluorine atoms to hydrogen atoms and adjusting the carbon-fluorine bond lengths. Pd-MOF contains $Pd^{2+}$ cations bonded to 2-hydroxypyrimidinolate linkers in a sodalite topology. The coordinated Pd atoms exist in a square planar configuration, and the MOF has pore diameters of approximately 0.22, 0.49, and 0.58 nm, FIG. 22.

Grand canonical Monte Carlo (GCMC) calculations were performed to simulate adsorption in these MOFs.[31,32] A total of 50,000 equilibration cycles and 250,000 production cycles were used for each simulation. One cycle consists of N moves, where N is the number of molecules (minimum of 20 moves). Insertion, deletion, translation, and identity change moves (e.g., change Xe to Kr) were considered. By dividing the production run into 5 independent blocks and calculating the standard deviation of the block averages, an average error of 1.3% in the loading is estimated at the 95% confidence interval. Using propagation of error, the selectivities reported have estimated errors of 1.8% at the 95% confidence interval. Single-component and mixture isotherms were simulated for each MOF. The mixture isotherms had a fixed 80/20 molar composition of krypton to xenon in the gas phase to be representative of an industrial mixture. Fugacities were calculated using the Peng-Robinson equation of state. Framework atoms were considered fixed at their crystallographic coordinates. This approximation of a rigid framework has been shown to be a reasonable strategy for screening adsorption in MOFs.[22] A 12-6 Lennard-Jones potential was used to describe sorbate-framework interactions. For the MOF atoms, van der Waals parameters were taken from the DREIDING[33] force field and, if not available, from the UFF[34] forcefield. This choice of forcefield has been effective in past studies of hydrogen and methane adsorption in IRMOF-1,[35,36] as well as $CO_2$ adsorption in a variety of MOFs.[37,38] A cutoff of 1.2 nm was used for the van der Waals interactions. Krypton[39] and xenon[40] parameters were obtained from the literature. Lorentz-Berthelot mixing rules were used for the gas/framework interactions. No electrostatic charges were considered. Selectivities from the mixture isotherms were calculated with the standard definition:

$$\text{Selectivity} = (x_{Xe}/y_{Xe})/(x_{Kr}/y_{Kr})$$

where $x_i$ is the adsorbed phase mole fraction of component i and $y_i$ is the gas phase mole fraction of component i. Additionally, in some cases we crudely predicted selectivities of mixture adsorption from the single-component isotherms by calculating the ratio of the amount of adsorbed Xe at a given pressure to the amount of adsorbed Kr at the same pressure. All simulations were performed at 273 K. All data reported are excess adsorption isotherms, which can be calculated using absolute adsorption values, pore volume, and bulk fluid density.[41] Also, IAST calculations were performed to determine whether single-component isotherms could be used to accurately predict the results from full mixture simulations.

Results

Figure 10:
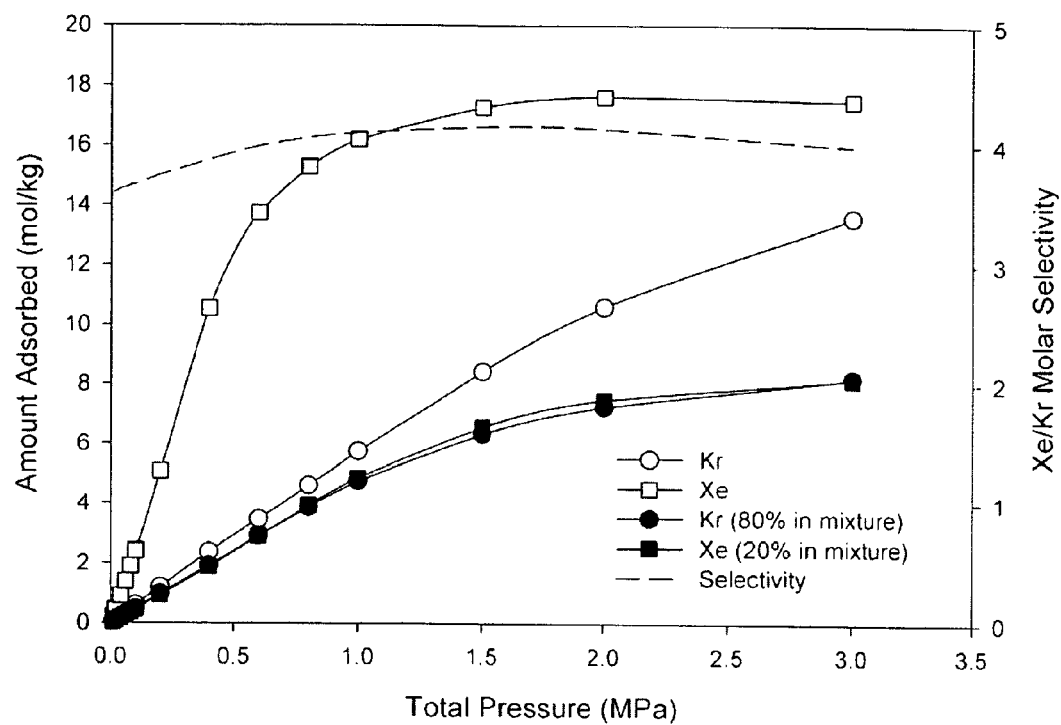
FIG. 10: Single component (open symbols) and mixture (filled symbols) isotherms for Xe and Kr adsorption in IRMOF-1 at 273 K. The Xe/Kr selectivity remains relatively constant at about 3.5-4 over this pressure range.
Figure 11:
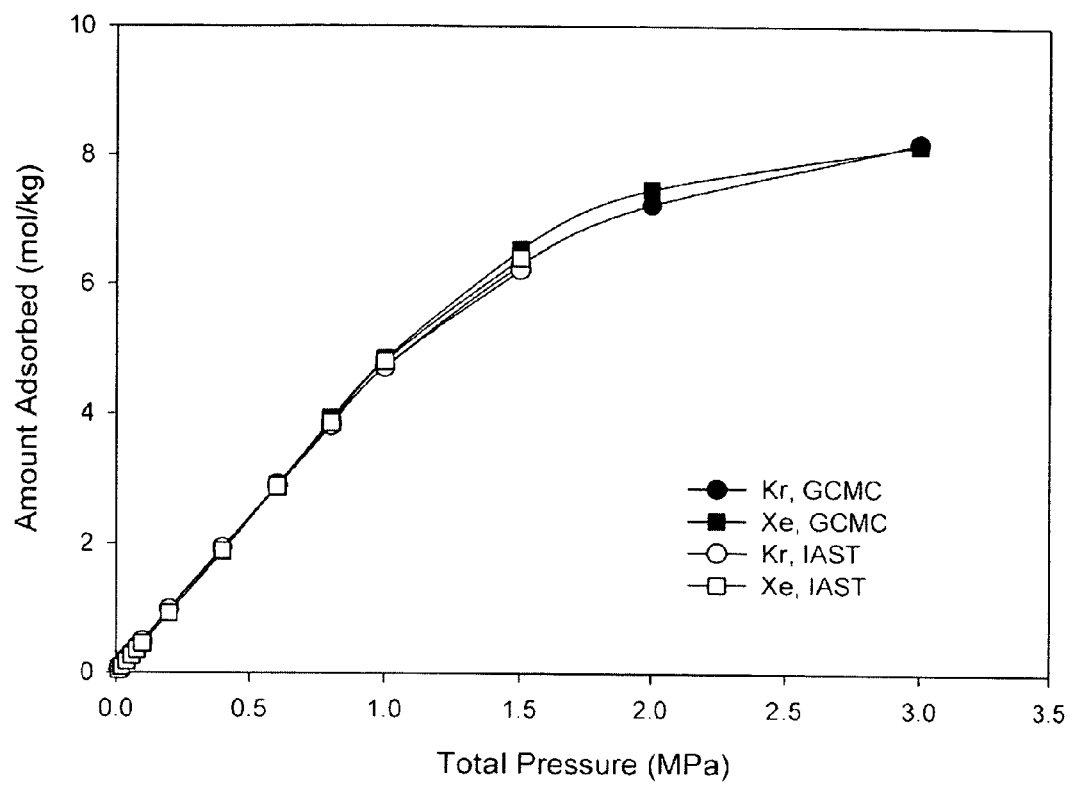
FIG. 11: Mixture isotherms (filled symbols) and those predicted by IAST (open symbols) for Xe and Kr adsorption in IRMOF-1 at 273 K. IAST reproduces the mixture results very well over the pressure range investigated.
Figure 13:
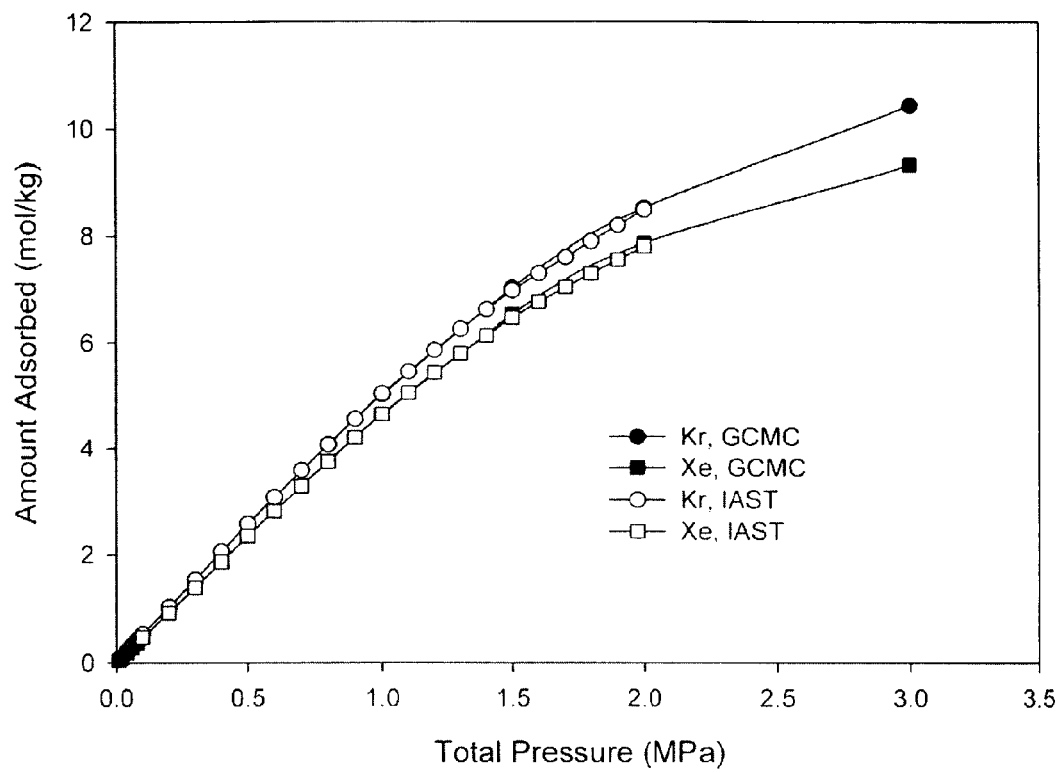
FIG. 13: Mixture isotherms (filled symbols) and those predicted by IAST (open symbols) for Xe and Kr adsorption in UMCM-1 at 273 K.

IRMOF-1 (also known as MOF-5) is probably the most studied MOF to date. The results for xenon and krypton adsorption in IRMOF-1 are comparable to the previous results from Greathouse et al.[22] (FIG. 10). Selectivities of about 3.5 to 4 for xenon over krypton are predicted, and this selectivity changes very little as a function of pressure. Adsorption in UMCM-1 also displays xenon selectivities of about 3.5 to 4, as shown in FIG. 1. Although the capacity of UMCM-1 is by far the largest of all MOFs investigated here (about 15 and 25 mol/kg in single-component isotherms for Kr and Xe, respectively), the xenon selectivity does not represent a significant improvement relative to previously reported values for zeolites. Density plots of mixture adsorption in UMCM-1 at 6 bar and at 273 K for Kr and Xe showed that the majority of adsorption is near the $Zn_4O$ corners and along the organic linkers. Density plots at 0.6 MPa suggest that xenon and krypton atoms adsorb next to organic linkers once stronger sites near the corners are filled, which is a mechanism that was previously found for other molecules in IRMOFs.[42] Note that before the simulation, the unit cell was divided into 150×150×150 voxels. After each cycle, the number of adsorbed molecules is counted, and their corresponding voxel values are updated accordingly. After normalization with respect to the highest occurring value in the histogram, the probability of finding an adsorbed molecule is represented). Additionally, crudely estimating selectivity of mixture adsorption from the single-component data allows one to obtain a good estimate of the xenon selectivity calculated explicitly from the mixture simulations. Adsorption in both IRMOF-1 and UMCM-1 follows IAST (FIGS. 11 and 13). Given the relatively modest selectivities in these large-pore MOFs, applicants thought it would be beneficial to study MOFs with smaller pore sizes where there are stronger adsorption sites to enhance the selectivity.

Figure 15:
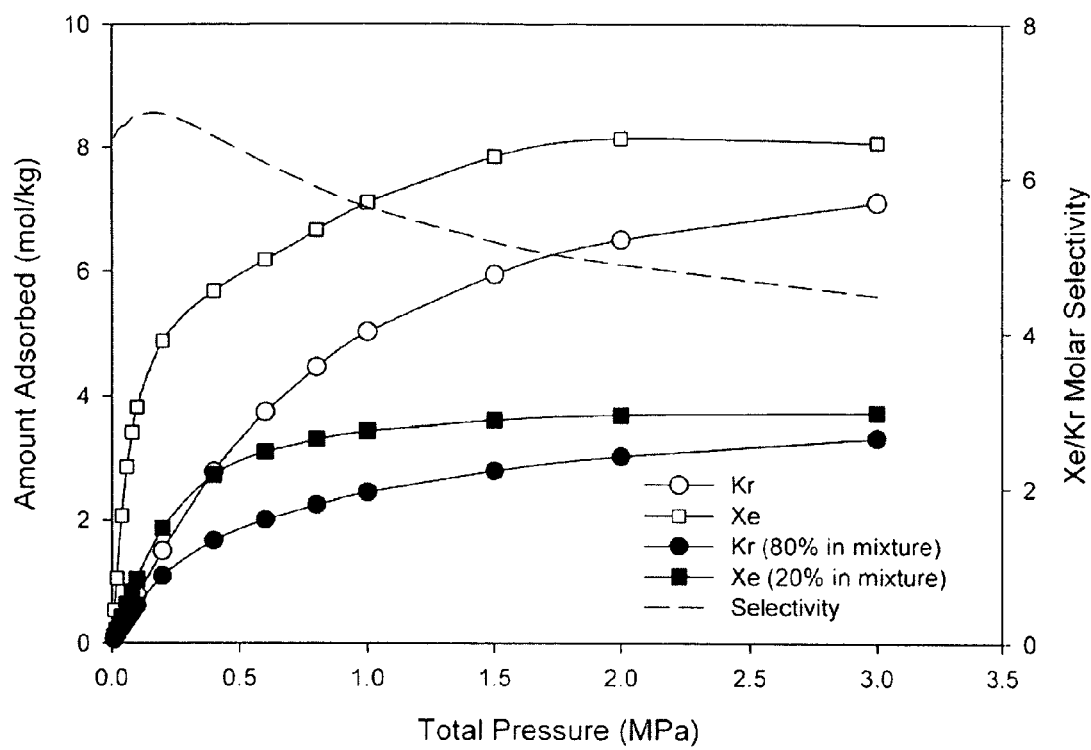
FIG. 15: Single component (open symbols) and mixture (filled symbols) isotherms for Xe and Kr adsorption in ZIF-8 at 273 K.
Figure 16:
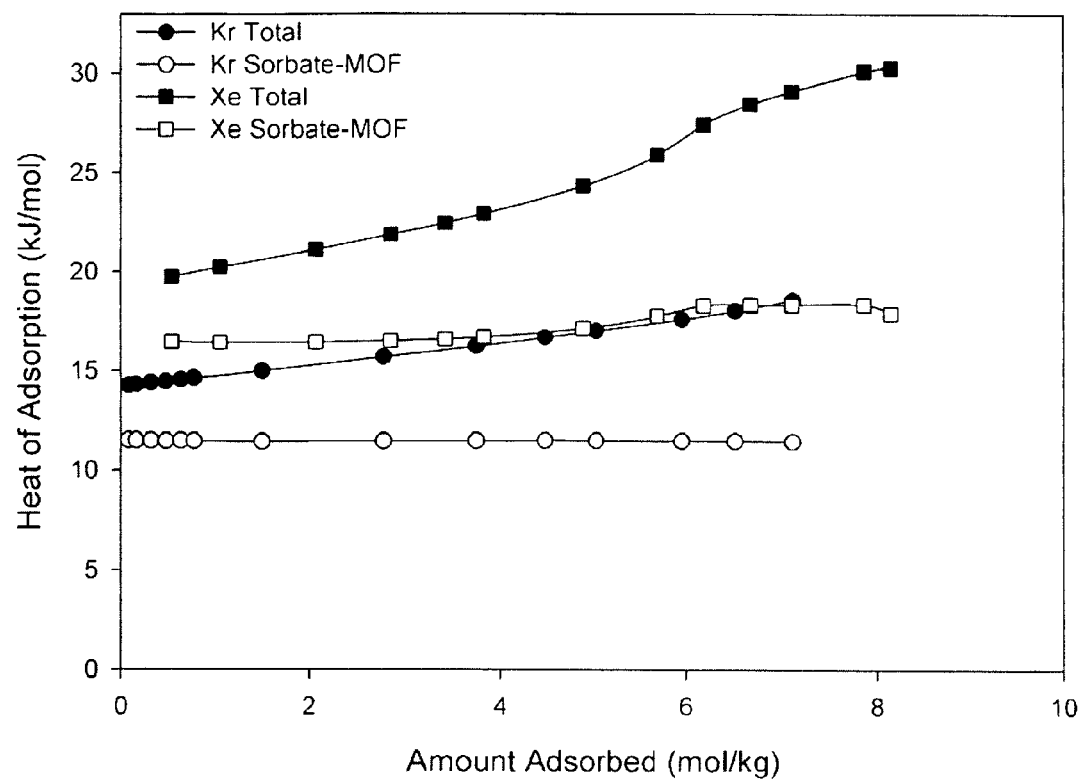
FIG. 16: Heats of adsorption versus loading for Kr (circles) and Xe (squares) single-component adsorption in ZIF-8 at 273 K as well as the sorbate-MOF contribution. The presence of attractive sorbate-sorbate interactions at higher loading is responsible for the gradual increase in isosteric heats.

This study is borne out by the mixture isotherms in ZIF-8 that show a maximum xenon selectivity of about 7 (FIG. 15). Its smaller pores yield stronger adsorption sites, which favor Xe binding and lead to an increase in selectivity. FIG. 16 shows the heats of adsorption for single components in ZIF-8. The heats of adsorption rise for both Xe and Kr with increasing loading, due to the increasing importance of sorbate-sorbate interactions. While the pores of ZIF-8 are smaller than those of IRMOF-1 and UMCM-1, the pore diameters of ZIF-8 are still large relative to the size of xenon and krypton (0.4100 and 0.3636 nm, respectively). This void space lacks adsorption sites that are strong enough to enhance xenon selectivity dramatically.

Figure 2:
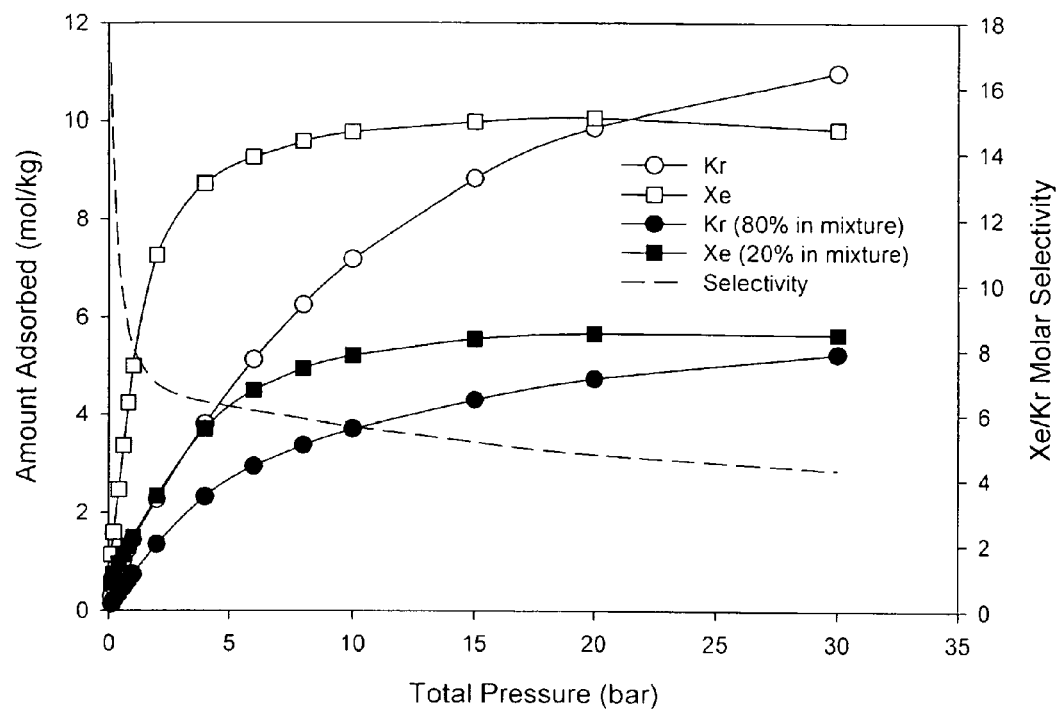
FIG. 2: Single-component (open symbols) and mixture (filled symbols) isotherms for Xe and Kr adsorption in HKUST-1 at 273 K. At low pressures (approximately 0.1 bar), the xenon selectivity is nearly 17, which is much higher than the selectivities estimated from the single-component isotherms.
Figure 3:
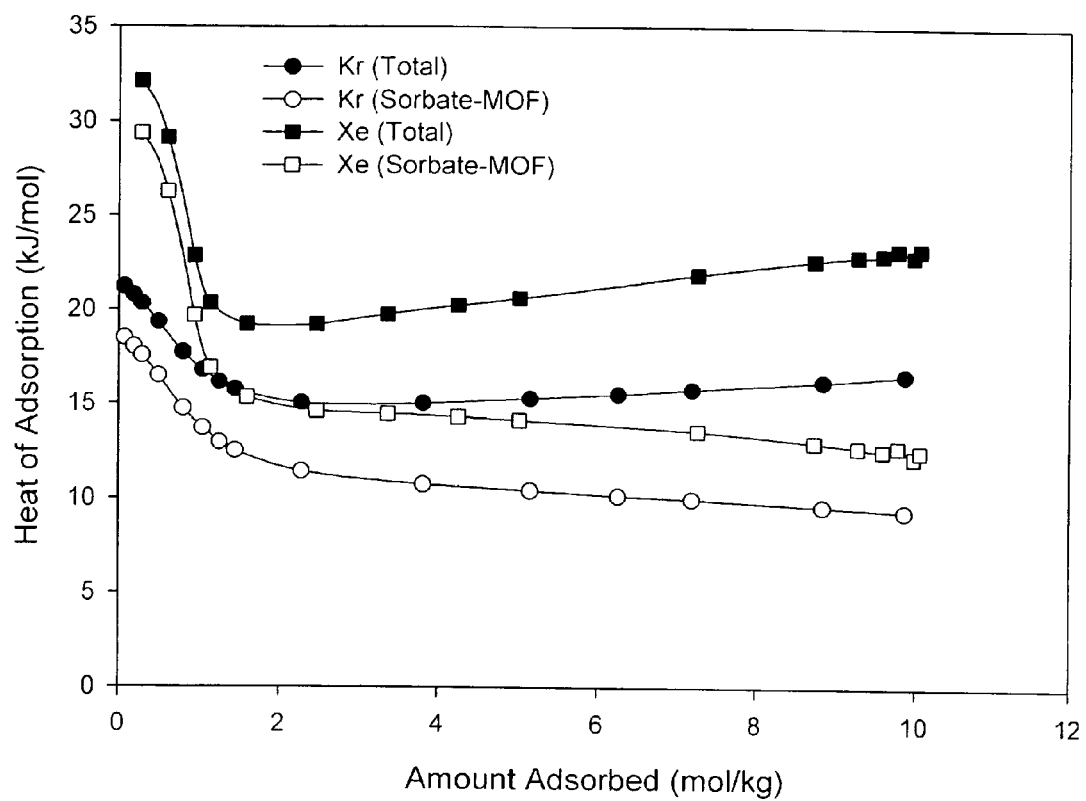
FIG. 3: Heats of adsorption versus loading for Kr (circles) and Xe (squares) single-component adsorption in HKUST-1 at 273 K, as well as averaged sorbate-MOF interaction energies. At low loading, adsorption in the small octahedral pockets leads to high heats of adsorption.
Figure 4:
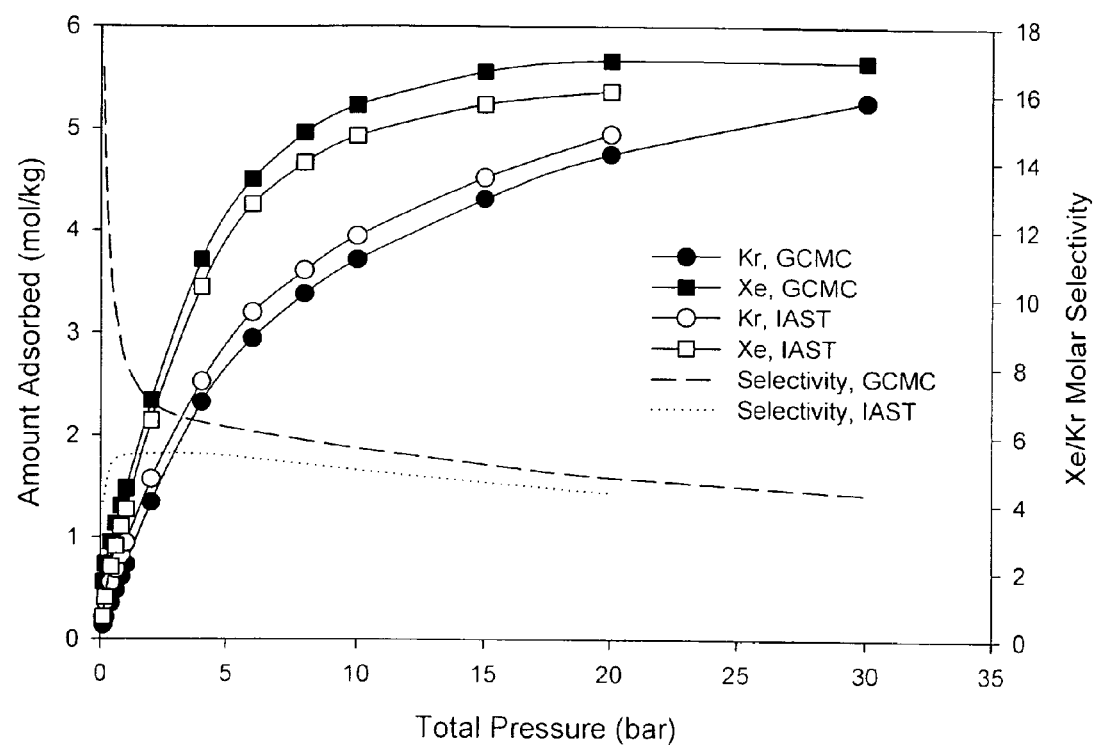
FIG. 4: Mixture isotherms from GCMC simulations (filled symbols) and isotherms predicted by IAST based on single-component isotherms (open symbols) for Xe and Kr adsorption in HKUST-1 at 273 K. IAST does not correctly predict Xe and Kr adsorption of the mixture results since it cannot correctly capture competitive adsorption in the octahedral pockets.

FIG. 2 shows the calculated isotherms for HKUST-1, which was previously tested experimentally as an adsorbent material for Xe/Kr separation.[21] Although binary adsorption selectivities naively estimated from the single-component isotherms are between 3 and 4 up to 0.1 MPa, mixture adsorption results predict much higher xenon selectivities: nearly 17 at 0.01 MPa and 8 at 0.1 MPa. Density plots revealed the cause of this large selectivity at low coverage. In single-component adsorption, both Kr and Xe prefer to adsorb in the small octahedral pockets since they are the strongest adsorption sites in the MOF. These pockets are so small that only one atom of Xe or Kr can fit inside. However, when a binary mixture is present, xenon and krypton directly compete for these strong binding sites. At low loading, heats of adsorption for krypton and xenon have values of 21 and 32 kJ/mol, respectively, which represents a significant increase relative to their values at marginally higher loading (FIG. 3). Due to stronger van der Waals interactions, xenon preferentially occupies this octahedral pocket and prevents krypton from adsorbing. Instead, krypton adsorbs near the pocket openings. Adsorption in HKUST-1 leads to significant deviation from IAST, which predicts xenon selectivities between 4 and 5 as shown in FIG. 4. This deviation is significant at low pressure, which is in contrast to most adsorption systems, where deviations from ideality are more common at higher loadings.

The phenomenon of high selectivity in very small pores is applied to picking candidate MOFs for Xe/Kr separation. That is, MOFs with adsorption sites that are large enough to accommodate a Xe atom but small enough to fit only one atom are attractive candidates. For example, while HKUST-1 showed preferential adsorption sites, the xenon selectivity drops considerably from 17 at 0.01 MPa to 8 at 0.1 MPa and nearly approaches that predicted by IAST around 1.0-1.5 MPa because of increased adsorption in the larger pores. These results show that although adsorption in the octahedral pockets is highly non-ideal, adsorption in the larger pores is ideal and increasingly contributes to the overall xenon selectivity as the pressure and gas loading are increased. Therefore, applicants examined other MOFs to identify those with smaller pores that also impart non-ideal adsorption and maintain enhanced xenon selectivity over a wider pressure range.

Figure 5:
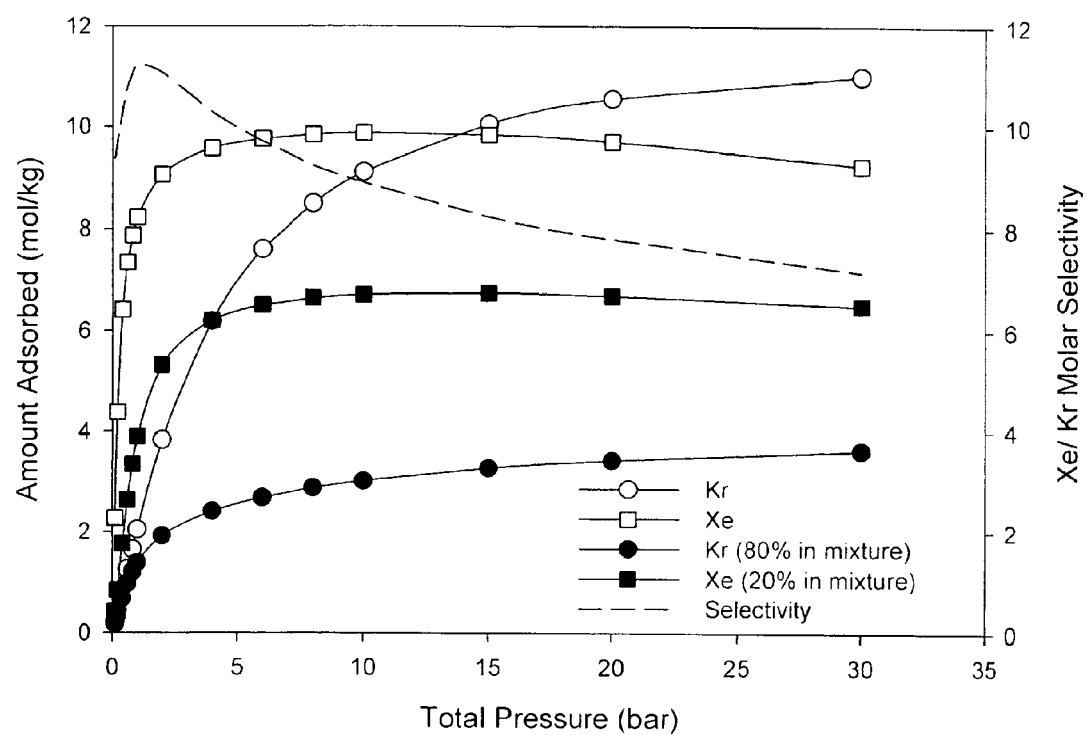
FIG. 5: Single-component (open symbols) and mixture (filled symbols) isotherms for Xe and Kr adsorption in MOF-505 at 273 K. Unlike HKUST-1, xenon selectivity remains elevated even at higher pressures, making it a promising candidate material for Xe/Kr separation.

One attractive candidate pursuant to the invention was MOF-505, which has smaller average pore sizes than HKUST-1. The simulation results for this MOF are shown in FIG. 5. The steepness of the single-component isotherms indicates that small pores are present and that adsorbed species have high heats of adsorption. Density plots revealed adsorption of xenon and krypton near the pore openings in the MOF. Compared to HKUST-1, MOF-505 has smaller cavity or pore sizes, Table 1 and FIG. 18, which allow the xenon selectivity to remain elevated over a wide pressure range (~9 at 1 MPa).

Referring to Table 1, MOF-505 has two out of three categories of pores (cavities) that allow Xe selectively by virtue of accommodating only a single Xe atom in each pore. In particular, MOF-505 material includes two categories of pores that have a pore size in the range of 0.45-0.75 nm; namely, pore sizes of 0.48 and 0.71 nm). From FIG. 18, it is apparent that about 46% of the total pore volume of MOF-505 is in this range in contrast to FIG. 17 for the HKUST-1 material, which has only about 12% of thee total pore volume in this range. Such MOF materials as MOF-505 can selectively adsorb Xe over Kr in a multi-component Xe—Kr mixture over a pressure range of 0.01 to 1.0 MPa.

Since typical pressure swing adsorption processes are run between 0.1 and 0.5 MPa, the selectivities of MOF-505 of about 10 to 11 in this pressure range are superior to those of HKUST-1 (about 6 to 8), making MOF-505 a more attractive MOF for Xe/Kr separation.

Figure 6:
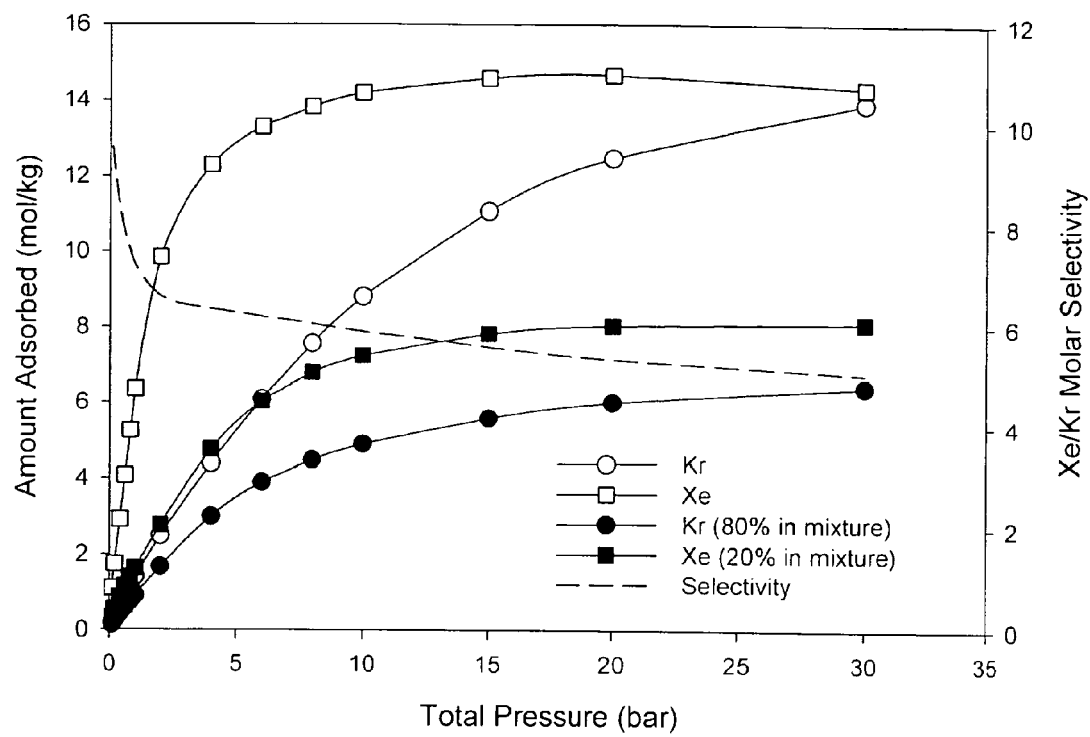
FIG. 6: Single-component (open symbols) and mixture (filled symbols) isotherms for Xe and Kr adsorption in NOTT-101 at 273 K. The extra phenyl moiety in the linker compared to MOF-505 makes the pore size too large and leads to lower selectivities relative to those predicted for MOF-505.
Figure 21:
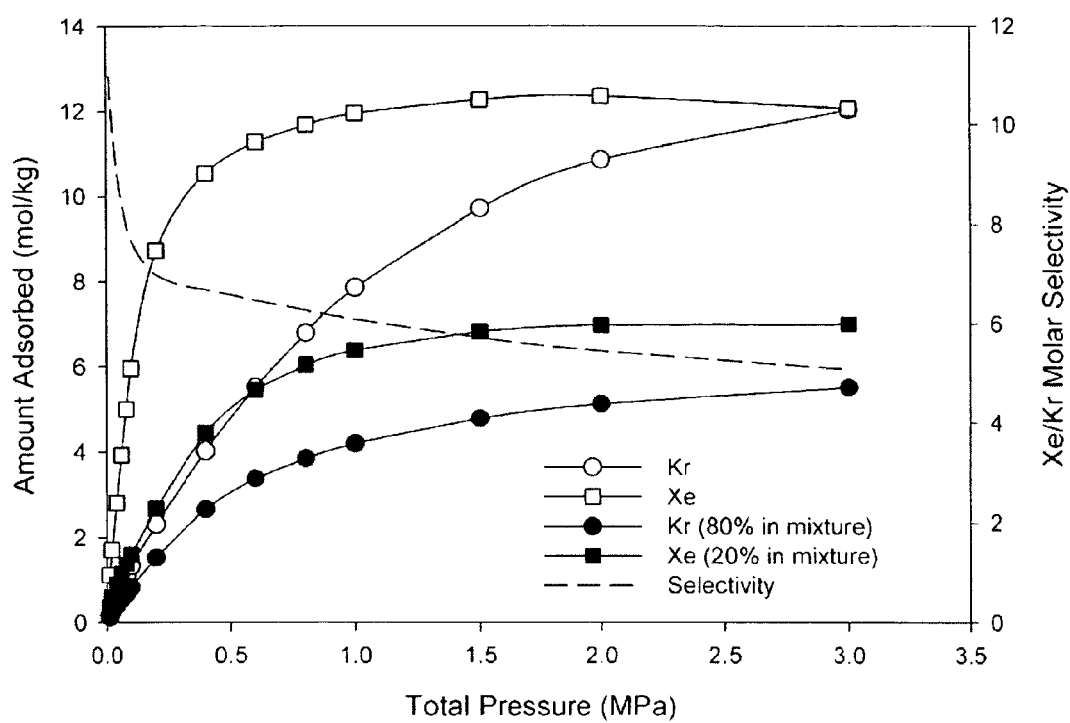
FIG. 21: Single-component (open symbols) and mixture (filled symbols) isotherms of Xe and Kr adsorption in NOTT-108 at 273 K.

In order to explore whether the enhanced selectivity of MOF-505 was due to pore size and not to framework topology, NOTT-101 and NOTT-108 were tested. These MOFs have the same topology as MOF-505, but are composed of slightly longer triphenyl linkers. FIG. 6 shows that the results follow a similar trend to those for HKUST-1, where a maximum selectivity of about 10 occurs at 0.01 MPa for the mixture isotherms and then decreases significantly with increasing pressure and gas loading (down to 5 at 3 MPa). The pore sizes of NOTT-101 are too large to ensure non-ideal adsorption at higher loadings. The results. FIG. 21, for NOTT-108 can be interpreted similarly and are not significantly different from those for NOTT-101 despite the presence of fluorine atoms on the organic linkers.

Figure 7:
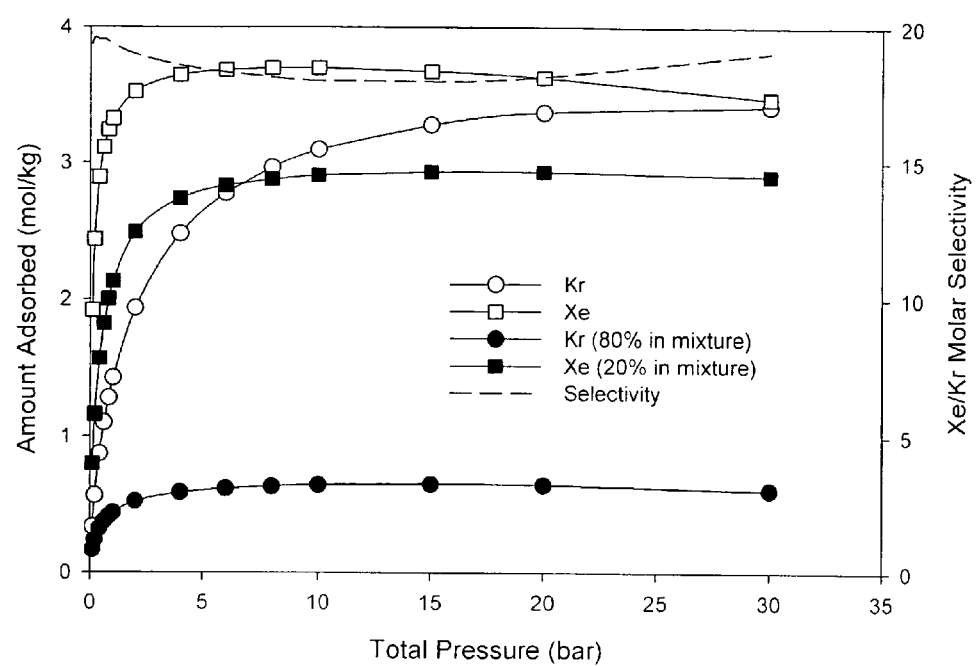
FIG. 7: Single-component (open symbols) and mixture (filled symbols) isotherms for Xe and Kr adsorption in Pd-MOF at 273 K.

Finally, applicants investigated Pd-MOF in order to test MOFs with even smaller pores. FIG. 7 displays the simulation results. The pores are so small that the xenon selectivity is very high, remaining near 18 or 19 for the entire pressure range from 0.01 to 3 MPa. Density plots revealed that Xe and Kr can only adsorb in the larger cavities of the MOF and not in the octahedral pockets, which are too small. Xenon dominates the adsorption at all pressures and prevents krypton from adsorbing, leading to the high selectivity. However, the adsorption capacities (up-take) of both Xe and Kr for Pd-MOF are significantly lower than those of the other MOFs. In fact, Pd-MOF had the lowest void fraction (0.348) of all MOFs investigated (void fractions of IRMOF-1=0.814; UMCM-1=0.871; ZIF-8=0.495; HKUST-1=0.746; MOF-505=0.741; NOTT-101=0.775; and NOTT-108=0.743). These results offer a preliminary estimate to the maximum xenon selectivity using competitive adsorption sites in MOFs.

Example

Breakthrough measurements were performed on MOF-505 material synthesized by the applicant. For example, 390 mg of MOF-505 pellets of pellet size of 600~1000 μm were packed into a stainless steel column with a length of 12 cm and an internal diameter of 0.46 cm, and the remaining volume in the column was filled by glass wool. Helium gas was used to initially purge the system. At a certain time (t=0), a mixture of containing 80 volume % Kr and 20 volume % Xe was introduced into the column at a flow rate of 10 ml/min. The flow rates of all gases were regulated by mass flow controllers, and the effluent gas stream from the column was monitored by mass spectroscopy (MS).

Figure 8:
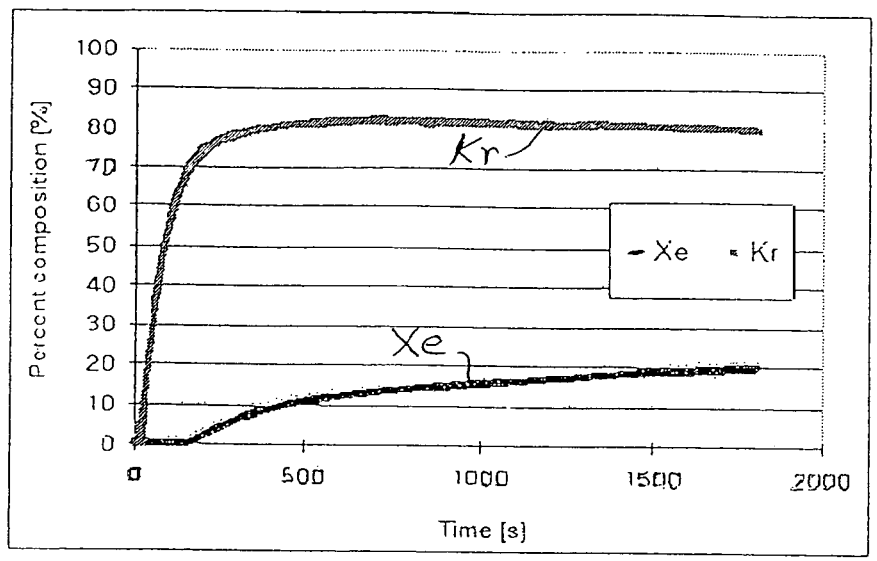
FIG. 8: Breakthrough curves for the separation of Xe/Kr mixtures (Xe:Kr=20: 80 vol. %) over MOF-505 pellets at room temperature. The total flow is 10 ml/min and the pressure is 1 bar.

The breakthrough result is shown in FIG. 8. Kr gas elutes rapidly from the column, whereas Xe is strongly retained. After an initial period during which both Xe and Kr are fully adsorbed, pure Kr elutes from the column. The effluent Kr concentration slightly exceeds the feed concentration because the more strongly retained Xe molecules displace some of the adsorbed Kr molecules. When the breakthrough of Xe at the column outlet starts, the effluent concentrations of the components evolve toward the feed concentration level as the column becomes saturated. The result of FIG. 8 demonstrates that MOF-505 has a high selectivity for Xe over Kr.

CONCLUSIONS

Applicants performed GCMC simulations of both single component and mixture adsorption of Xe and Kr in a variety of MOFs. The results are summarized in Table 3 below. Pd-MOF is predicted to have the largest selectivity, and the high selectivity is maintained across a wide range of pressures in this material. Large pore materials are not desirable for efficient Xe/Kr separation. Both IRMOF-1 and UMCM-1 show low xenon selectivities of about 4 and follow ideal adsorption. To enhance selectivity, small pores or pockets are needed to preferably bind Xe instead of Kr and introduce non-ideality to mixture adsorption. HKUST-1 has a high adsorptive selectivity at low loading due to its small pockets where Xe atoms adsorb with higher heats of adsorption than Kr. However, the selectivities in HKUST-1 drop off quickly at higher pressure due to the presence of large cavities or pores, which are filled after the small octahedral pockets, demonstrating that the best MOFs for Xe/Kr separation should have relatively high percentages of small cavity sizes such as 20% or more, preferably 40% or more, of small cavity sizes (e.g. 0.45-0.75 nm diameter).

MOF-505 has three types of pores with two out of three (about 46% of total pore volume) being relatively small in the range of 0.48 to 0.71 nm diameter. This MOF maintains its elevated xenon selectivities over a large pressure range as shown in the Example above.

NOTT-101 and NOTT-108 share the same topology with MOF-505 but have pores that are too large for efficient Xe/Kr separation.

TABLE 3

Xe/Kr selectivity for all MOFs investigated at pressures of 0.1 bar, 1 bar, and 10 bar as predicted from mixture simulations at 273 K.

| MOF | Xe/Kr Selectivity | | |
|---|---|---|---|
| | 0.1 bar | 1 bar | 10 bar |
| IRMOF-1 | 3.6 | 3.7 | 4.1 |
| UMCM-1 | 3.5 | 3.6 | 3.7 |
| ZIF-8 | 6.5 | 6.8 | 5.6 |
| HKUST-1 | 16.8 | 8.1 | 5.6 |
| MOF-505 | 9.4 | 11.2 | 8.9 |
| NOTT-101 | 9.6 | 7.2 | 5.9 |
| NOTT-108 | 11.0 | 7.7 | 6.1 |
| Pd-MOF | 19.4 | 19.4 | 18.0 |

Practice of the present invention may replace cryogenic distillation as the preferred method for separating noble gases. The MOF adsorbent materials could be used as adsorbents in a pressure swing adsorption process, which is much less energy intensive than distillation. Additionally, the enhanced selectivities obtained with MOFs compared to zeolites may allow for the treatment of spent nuclear fuel and increase the industrial supply of xenon. Currently, high levels of radioactive krypton-85 prevent these waste gases from further use.

Although the invention has been described in connection with certain embodiment, those skilled in the art will appreciate that changes and modifications can made therein without departing from the spirit and scope of the invention as set forth in the appended claims.

REFERENCES WHICH ARE INCORPORATED HEREIN BY REFERENCE

1. Kerry F G. Industrial Gas Handbook: Gas Separation and Purification. Boca Raton, Fla.: CRC Press, 2007.
2. Izumi J. Waste gas treatment using zeolites in nuclear-related industries. In: Auerbach S M, Carrado K A, Dutta P K, eds. Handbook of Zeolite Science and Technology. New York, N.Y.: Marcel Dekker, 2003.
3. Jameson C J, Jameson A K, Lim H M. Competitive adsorption of xenon and krypton in zeolite NaA: Xe-129 nuclear magnetic resonance studies and grand canonical Monte Carlo simulations. J Chem. Phys. 1997; 107:4364-4372.
4. Rowsell J L C, Yaghi O M. Metal-organic frameworks: a new class of porous materials. Micropor Mesopor Mater. 2004; 73:3-14.
5. Ferey G. Hybrid porous solids: Past, present, future. Chem Soc Rev. 2008; 37:191-214.
6. Kitagawa S, Kitaura R, Noro S. Functional porous coordination polymers. Angew Chem Int Ed. 2004; 43:2334-2375.
7. Rowsell J L, Yaghi O M. Strategies for hydrogen storage in metal-organic frameworks. Angew Chem Int Ed. 2005; 44:4670-4679.
8. Hirscher M, Panella B. Hydrogen storage in metal-organic frameworks. Scripta Mater. 2007; 56:809-812.
9. Murray L J, Dinca M, Long J R. Hydrogen storage in metal-organic frameworks. Chem Soc Rev. 2009; 38:1294-1314.

10. Liu B, Yang Q, Xue C, Zhong C, Chen B, Smit B. Enhanced adsorption selectivity of hydrogen/methane mixtures in metal-organic frameworks with interpenetration: A molecular simulation study. J Phys Chem C. 2008; 112:9854-9860.

11. Li J R, Kuppler R J, Zhou H C. Selective gas adsorption and separation in metal-organic frameworks. Chem Soc Rev. 2009; 38:1477-1504.

12. Lee J, Farha O K, Roberts J, Scheidt K A, Nguyen S T, Hupp J T. Metal-organic framework materials as catalysts. Chem Soc Rev. 2009; 38:1450-1459.

13. Shultz A M, Farha O K, Hupp J T, Nguyen S T. A catalytically active, permanently microporous MOF with metalloporphyrin struts. J Am Chem. Soc. 2009;131:4204-4205.

14. Cho S H, Ma B Q, Nguyen S T, Hupp J T, Albrecht-Schmitt T E. A metal-organic framework material that functions as an enantioselective catalyst for olefin epoxidation. Chem. Commun. 2006:2563-2565.

15. Bae Y S, Mulfort K L, Frost H, Ryan P, Punnathanam S, Broadbelt L J, Hupp J T, Snurr R Q. Separation of CO2 from CH4 using mixed-ligand metal-organic frameworks. Langmuir. 2008; 24:8592-8598.

16. Bae Y S, Farha O K, Hupp J T, Snurr R Q. Enhancement of CO2/N2 selectivity in a metal-organic framework by cavity modification. J Mater Chem. 2009; 19:2131-2134.

17. Pan L, Olson D H, Ciemnolonski L R, Heddy R, Li J. Separation of hydrocarbons with a microporous metal-organic framework. Angew Chem Int Ed. 2006; 45:616-619.

18. Hartmann M, Kunz S, Himsl D, Tangermann O, Ernst S, Wagener A. Adsorptive separation of isobutene and isobutane on Cu3(BTC)2. Langmuir: 2008; 24:8634-8642.

19. Yang Q Y, Zhong C L. Molecular simulation of carbon dioxide/methane/hydrogen mixture adsorption in metal-organic frameworks. J Phys Chem B. 2006; 110:17776-17783.

20. Yang Q Y, Xue C Y, Zhong C L, Chen J F. Molecular simulation of separation of CO2 from flue gases in Cu-BTC metal-organic framework. AlChE J. 2007; 53:2832-2840.

21. Mueller U, Schubert M, Teich F, Puetter H, Schierle-Arndt K, Pastre J. Metal-organic frameworks—prospective industrial applications. J Mater Chem. 2006; 16:626-636.

22. Greathouse J A, Kinnibrugh T L, Allendorf M D. Adsorption and separation of noble gases by IRMOF-1: Grand canonical Monte Carlo simulations. Ind Eng Chem. Res. 2009; 48:3425-3431.

23. Eddaoudi M, Kim J, Rosi N, Vodak D, Wachter J, O'Keeffe M, Yaghi O M. Systematic design of pore size and functionality in isoreticular MOFs and their application in methane storage. Science. 2002; 295:469-472.

24. Koh K, Wong-Foy A G, Matzger A J. A crystalline mesoporous coordination copolymer with high microporosity. Angew Chem Int Ed. 2008; 47:677-680.

25. Park K S, Ni Z, Cote A P, Choi J Y, Huang R D, Uribe-Romo F J, Chae H K, O'Keeffe M, Yaghi O M. Exceptional chemical and thermal stability of zeolitic imidazolate frameworks. Proc Natl Acad Sci USA. 2006; 103:10186-10191.

26. Chui S S Y, Lo S M F, Charmant J P H, Orpen A G, Williams I D. A chemically functionalizable nanoporous material [Cu3(TMA)2(H2O)3]n. Science. 1999; 283: 1148-1150.

27. Chen B L, Ockwig N W, Millward A R, Contreras D S, Yaghi O M. High H2 adsorption in a microporous metal-organic framework with open metal sites. Angew Chem Int Ed. 2005; 44:4745-4749.

28. Lin X, Telepeni I, Blake A J, Dailly A, Brown C M, Simmons J M, Zoppi M, Walker G S, Thomas K M, Mays T J, Hubberstey P, Champness N R, Schroder M. High capacity hydrogen adsorption in Cu(II) tetracarboxylate framework materials: The role of pore size, ligand functionalization, and exposed metal sites. J Am Chem. Soc. 2009; 131:2159-2171.

29. Xamena FXLI, Abad A, Corma A. Garcia H. MOFs as catalysts: Activity, reusability and shape-selectivity of a Pd-containing MOF. J. Catal. 2007; 250:294-298.

30. Bohlmann W, Poppl A, Sabo M, Kaskel S. Characterization of the metal-organic framework compound $Cu_3$(benzene 1,3,5-tricarboxylate)$_2$ by means of 129Xe nuclear magnetic and electron paramagnetic resonance spectroscopy. J Phys Chem B. 2006; 110:20177-20181.

31. Snurr R Q, Yazaydin A O, Dubbeldam D, Frost H. Molecular modeling of metal-organic frameworks. In: MacGillivray L, ed. Metal-Organic Frameworks: Design and Application: Wiley-VCH, 2010.

32. Düren T, Bae Y S, Snurr R Q. Using molecular simulation to characterise metal-organic frameworks for adsorption applications. Chem Soc Rev. 2009; 38:1237-1247.

33. Mayo S L, Olafson B D, Goddard W A. Dreiding—A generic force-field for molecular simulations. J Phys Chem. 1990; 94:8897-8909.

34. Rappe A K, Casewit C J, Colwell K S, Goddard W A, Skiff W M. Uff, a full periodic-table force-field for molecular mechanics and molecular-dynamics simulations. J Am Chem. Soc. 1992; 114:10024-10035.

35. Ryan P, Broadbelt L J, Snurr R Q. Is catenation beneficial for hydrogen storage in metal-organic frameworks? Chem. Commun. 2008:4132-4134.

36. Duren T, Sarkisov L, Yaghi O M, Snurr R Q. Design of new materials for methane storage. Langmuir. 2004; 20:2683-2689.

37. Walton K S, Millward A R. Dubbeldam D. Frost H. Low J J, Yaghi O M. Snurr R Q. Understanding inflections and steps in carbon dioxide adsorption isotherms in metal-organic frameworks. J Am Chem. Soc. 2008; 130:406-407.

38. Yazaydin A O, Benin A I, Faheem S A, Jakubczak P, Low J J, Willis R R, Snurr R Q. Enhanced CO2 adsorption in metal-organic frameworks via occupation of open-metal sites by coordinated water molecules. Chem. Mater. 2009; 21:1425-1430.

39. Talu O, Myers A L. Reference potentials for adsorption of helium, argon, methane, and krypton in high-silica zeolites. Colloids Surf. A. 2001; 187:83-93.

40. Hirschfelder J O, Curtiss C F, Bird R B. Molecular Theory of Gases and Liquids. New York: Wiley, 1965.

41. Myers A L, Monson P A. Adsorption in porous materials at high pressure: Theory and experiment. Langmuir. 2002; 18:10261-10273.

42. Frost H, Düren T, Snurr R Q. Effects of surface area, free volume, and heat of adsorption on hydrogen uptake in metal-organic frameworks. J Phys Chem B. 2006; 110: 9565-9570.

43. Murthi M, Snurr R Q. Effects of molecular siting and adsorbent heterogeneity on the ideality of adsorption equilibria. Langmuir. 2004; 20:2489-2497.

44. Van Tassel P R, Davis H T, McCormick A V. Adsorption simulations of small molecules and their mixtures in a zeolite micropore. Langmuir. 1994; 10:1257-1267.

45. Keffer D, Davis H T, McCormick A V. Effect of loading and nanopore shape on binary adsorption selectivity. J Phys Chem. 1996; 100:638-645.

The invention claimed is:

1. A method of separating Xe and another noble gas in a gas mixture, comprising contacting the gas mixture with an adsorbent material comprising a metal-organic framework (MOP) material wherein the MOF material has 20% or more of the total pore volume of a size to receive no more than one Xe atom for selectively adsorbing Xe from the gas mixture,
   wherein selectivity of the MOF material for Xe from the gas mixture is about 9 to about 11 over a pressure range of 0.01 to 1.0 MPa at 273 K.

2. The method of claim 1 wherein the MOF material has 40% or more of the total pore volume in a pore size range of 0.45-0.75 nm.

3. The method of claim 1 wherein the MOF material has carboxylate linkers.

4. The method of claim 1 wherein the other noble gas is selected from the group consisting of Kr and Ar.

5. A method of separating Xe and another noble gas in a gas mixture, comprising contacting the gas mixture with an adsorbent material comprising a metal-organic framework (MOF) material wherein the MOF material has 20% or more of the total pore volume of a size to receive no more than one Xe atom for selectively adsorbing Xe from the gas mixture,
   wherein the MOF material exhibits a selectivity for Xe from the gas mixture of about 9 and 11 over a pressure range of 0.01 to 1.0 MPa at 273 K.

* * * * *